(12) United States Patent
Wagner

(10) Patent No.: US 11,813,192 B1
(45) Date of Patent: Nov. 14, 2023

(54) ORAL DEVICES

(71) Applicant: SLOW WAVE, INC., Houston, TX (US)

(72) Inventor: Wayne R. Wagner, Spicewood, TX (US)

(*) Notice: Subject to any disclaimer, the term of this patent is extended or adjusted under 35 U.S.C. 154(b) by 568 days.

(21) Appl. No.: 16/912,367

(22) Filed: Jun. 25, 2020

Related U.S. Application Data

(60) Provisional application No. 62/869,528, filed on Jul. 1, 2019.

(51) Int. Cl.
| | |
|---|---|
| *A61F 5/56* | (2006.01) |
| *B33Y 10/00* | (2015.01) |
| *B33Y 50/02* | (2015.01) |
| *B33Y 80/00* | (2015.01) |

(52) U.S. Cl.
CPC ............ *A61F 5/566* (2013.01); *B33Y 10/00* (2014.12); *B33Y 50/02* (2014.12); *B33Y 80/00* (2014.12)

(58) Field of Classification Search
CPC ......... A61F 5/566; B33Y 10/00; B33Y 50/02; B33Y 80/00
See application file for complete search history.

(56) References Cited

U.S. PATENT DOCUMENTS

| | | |
|---|---|---|
| 3,132,647 A | 5/1964 | Corniello |
| 3,434,470 A | 3/1969 | Strickland |
| 4,304,227 A | 12/1981 | Samelson |

(Continued)

FOREIGN PATENT DOCUMENTS

| | | |
|---|---|---|
| EP | 1205157 A1 | 5/2002 |
| EP | 1203570 B1 | 11/2011 |

(Continued)

OTHER PUBLICATIONS

Bailey, Premarket Notification [510(k)] Summary K013049 for mandibular repositioning appliance (device) known as NOrAD(TM), clearance granted by United States FDA, Nov. 29, 2001.

(Continued)

*Primary Examiner* — Rick K Chang
(74) *Attorney, Agent, or Firm* — Jeffrey L. Wendt; WENDT FIRM, P.C.

(57) ABSTRACT

Apparatus for reducing obstructive sleep apnea, snoring and/or nasal drainage, or improving sleep even without substantial reduction in snoring. One apparatus includes an upper member fitting portions of the interior and exterior surfaces of a user's upper dentition, and a lower member fitting similarly adjacent a user's lower dentition. The upper and lower members include molar and pre-molar extensions so that when the user bites or clenches, the upper right and lower right extensions impinge on one another in substantially overlapping fashion, as do the upper left and lower left extensions. In certain embodiments, patterned surfaces on mating right and left molar and pre-molar extensions reduce friction. The lower and upper molar and pre-molar extensions may have curved or arcuate shaped interior surfaces to provide more room for a user's tongue. Right and left sub-chambers formed in the upper and lower molar and pre-molar extensions may provide lateral space for the tongue. The oral devices may be produced by additive or subtractive manufacturing methods.

8 Claims, 18 Drawing Sheets

(56) References Cited

U.S. PATENT DOCUMENTS

| | | |
|---|---|---|
| 4,396,373 A | 8/1983 | Dellinger |
| 4,531,916 A | 7/1985 | Scantlebury et al. |
| 4,671,767 A | 6/1987 | Blechman et al. |
| 4,676,240 A | 6/1987 | Gardy |
| 4,700,697 A | 10/1987 | Mundell et al. |
| 4,708,646 A | 11/1987 | Jasper |
| 4,715,368 A | 12/1987 | George |
| 4,901,737 A | 2/1990 | Toone |
| 5,013,243 A | 5/1991 | Tanaka et al. |
| 5,056,534 A | 10/1991 | Wright |
| 5,117,816 A | 6/1992 | Shapiro et al. |
| 5,239,995 A | 8/1993 | Estes et al. |
| 5,499,633 A | 3/1996 | Fenton |
| RE35,295 E | 7/1996 | Estes et al. |
| 5,570,704 A | 11/1996 | Buzzard et al. |
| 5,611,355 A | 3/1997 | Hilsen |
| 5,678,998 A | 10/1997 | Honkura et al. |
| 5,683,244 A | 11/1997 | Truax |
| 5,692,521 A | 12/1997 | Leasure-Nelson |
| 6,074,207 A | 6/2000 | Coats |
| 6,082,363 A | 7/2000 | Washburn |
| 6,109,265 A | 8/2000 | Frantz et al. |
| 6,213,959 B1 | 4/2001 | Kushida |
| 6,299,450 B1 | 10/2001 | Honkura et al. |
| 6,427,689 B1 | 8/2002 | Estes |
| 6,491,037 B1 | 12/2002 | Mortenson |
| 6,505,625 B1 | 1/2003 | Uenishi |
| 6,659,771 B2 | 12/2003 | Honkura et al. |
| 6,766,802 B1 | 7/2004 | Keropian |
| 7,107,992 B2 | 9/2006 | Brooks et al. |
| 7,178,529 B2 | 2/2007 | Kownacki |
| 7,225,021 B1 | 5/2007 | Park et al. |
| 7,255,110 B2 | 8/2007 | Knudson et al. |
| 7,322,356 B2 | 1/2008 | Critzer et al. |
| 7,451,767 B2 | 11/2008 | Keropian |
| 7,540,843 B2 | 6/2009 | De Backer |
| 7,607,439 B2 | 10/2009 | Li |
| 7,637,262 B2 | 12/2009 | Bailey |
| 7,712,468 B2 | 5/2010 | Hargadon |
| 7,810,502 B1 | 10/2010 | Nguyen et al. |
| 8,061,358 B2 | 11/2011 | Smernoff |
| 8,215,312 B2 | 7/2012 | Garabadian et al. |
| 8,257,079 B1 | 9/2012 | Plowman |
| 8,272,866 B2 | 9/2012 | Chun et al. |
| 8,875,713 B2 | 11/2014 | Metz |
| 8,881,733 B1 | 11/2014 | Harkins |
| 9,144,512 B2 | 9/2015 | Wagner |
| 9,204,991 B1 | 12/2015 | Harkins |
| 9,408,743 B1 | 8/2016 | Wagner |
| 9,439,802 B2 | 9/2016 | Wagner |
| 9,445,938 B1 | 9/2016 | Wagner |
| 10,299,957 B2 | 5/2019 | Wagner |
| 2001/0027793 A1 | 10/2001 | Tielmans |
| 2004/0177852 A1 | 9/2004 | Abramson |
| 2005/0121039 A1 | 6/2005 | Brooks et al. |
| 2005/0236003 A1 | 10/2005 | Meader |
| 2006/0252685 A1 | 11/2006 | Gould |
| 2006/0289013 A1 | 12/2006 | Keropian |
| 2007/0283967 A1 | 12/2007 | Bailey |
| 2008/0060660 A1 | 3/2008 | Nelson et al. |
| 2008/0173312 A1 | 7/2008 | Peake et al. |
| 2008/0199824 A1 | 8/2008 | Hargadon |
| 2008/0210244 A1 | 9/2008 | Keropian |
| 2008/0257358 A1 | 10/2008 | Stern et al. |
| 2008/0264422 A1 | 10/2008 | Fishman |
| 2008/0276938 A1 | 11/2008 | Jeppesen et al. |
| 2009/0036889 A1 | 2/2009 | Callender |
| 2009/0056724 A1 | 3/2009 | Keropian |
| 2009/0120448 A1 | 5/2009 | Keropian |
| 2009/0188510 A1 | 7/2009 | Palmer |
| 2010/0211184 A1 | 8/2010 | Rousseau et al. |
| 2010/0224197 A1 | 9/2010 | Keropian |
| 2010/0300458 A1 | 12/2010 | Stubbs et al. |
| 2014/0261464 A1* | 9/2014 | Layzell ............... A63B 71/085 128/861 |

FOREIGN PATENT DOCUMENTS

| | | |
|---|---|---|
| WO | WO 2007/134375 | 11/2007 |
| WO | WO 2010/040026 | 4/2010 |
| WO | WO 2010/062952 | 6/2010 |
| WO | WO 2010/093264 | 8/2010 |

OTHER PUBLICATIONS

Bailey, Premarket Notification [510(k)] Summary K020893 for mandibular repositioning appliance (device) known as NOrAD(TM), clearance granted by United States FDA, May 28, 2002.

Britishsnoring; Tomed SomnoGuard FittingHeated for 20 seconds, YouTube video, uploaded to the Internet by britishsnoring on Apr. 26, 2010, http://www.youtube.com/watch?v=OXfN76M2l1A.

Department of Health & Human Services; K964516; Letter to James Bonds of Nellcor Puritan Bennett, Incorporated; Jun. 2, 2005; Rockville, MD; US.

Dynasplint; Wearing your Jaw Dynasplint® System, YouTube video, uploaded to the Internet by dynasplint on Oct. 5, 2011, http://www.youtube.com/watch?v=3hjP24aByd4.

European Patent Office; "Invitation to Pay Additional Fees and, Where Applicable, Protest Fee" for PCT/US2012/036474; dated Jul. 25, 2012; Rijswijk; Netherlands.

European Patent Office; International Search Report for PCT/US2012/036474; 6 pages, dated Sep. 9, 2012; Rijswijk, Netherlands.

European Patent Office; Written Opinion of the International Searching Authority for PCT/US2012/036474, 12 pages, dated Sep. 9, 2012; Munich, Germany.

FDA 510(k) Summary K033822, Feb. 6, 2004.

FDA 510(k) Summary K033823, Feb. 6, 2004.

FDA 510(k) Summary K042161, Oct. 27, 2004.

FDA 510(k) Summary K061688, Sep. 8, 2006.

FDA 510(k) Summary K102118, Sep. 8, 2010; Ranir, LLC, 510(k) Summary K102118 for Intraoral Anti-Snoring Device known as Snore Guard Advance(TM), clearance granted by United States FDA, Sep. 8, 2010.

FDA 510(k) Summary K121761, Sep. 28, 2012.

FDA 510(k) Summary K962516, Sep. 10, 1996.

FDA 510(k) Summary K972061, Aug. 21, 2007; Thornton; Non-Confidential Summary of Safety and Effectiveness; K972061; Aug. 21, 1997; Dallas, TX; US.

FDA 510(k) Summary; Wagner Direct; FDA 501K Summary; Apr. 15, 2014; Houston, Texas; US.

Hoffstein; "Review of oral appliances for treatment of sleep-disordered breathing", Sleep Breath (2007) 11 :1-22, published online Nov. 29, 2006, Springer-Verlag; Germany.

Houston-Chronicle; "Tired of Your CPAP?", Jan. 16, 2011.

I Hate CPAP!; "Sleep Apnea Appliances, I Hate CPAP!", p. 1-8, downloaded from the Internet Oct. 25, 2010; http://www.ihatecpap.com/oral_appliances.html'; Illinois; US.

Landers, SJ, "Link strengthened between sleep apnea and mortality risk", amednews, Sep. 1, 2008; American Medical Association; US.

Pancer, et al., "Evaluation of Variable Mandibular Advancement Appliance for Treatment of Snoring and Sleep Apnea", Chest (1999); 116:1511-1518; Clinical Investigations; US.

Prehn, Ronald S "What is a Mandibular Advancement Splint and How Does it Work?", YouTube video, uploaded to the Internet by rsprehn on Mar. 4, 2010, http://www.youtube.com/watch?v=OWiQQF4xQZc.

Randerath et al., "Non-CPAP therapies in obstructive sleep apnea", Eur Respir J (no month, 2011); vol. 37, No. 5; pp. 1000-1028; Paris, France.

Sybron Dental Specialties; 510(k) Summary K070327 for Intraoral Devices for Snoring and Intraoral Devices for Snoring and Obstructive Sleep Apnea known as Removable Acrylic Herbst(TM), Allesee Snore Appliance(TM), and Enoch Snorinator(TM), clearance granted by United States FDA, May 25, 2007; Sturtevant, WI; US.

Somnomed; Sleep Apnea Appliances; I hate CPAP; Oct. 25, 2010; 8 pages; US.

Response to Office Action for U.S. Appl. No. 14/852,768, filed Jun. 13, 2016, with Terminal Disclaimer; 7 pages.

(56) References Cited

OTHER PUBLICATIONS

Office Action for U.S. Appl. No. 14/852,768 dated Jun. 3, 2016; 8 pages.
Amendment after Allowance for U.S. Appl. No. 13/456,682, filed Aug. 15, 2015; 7 pages.
Amendment and Response for U.S. Appl. No. 13/456,682, filed Feb. 18, 2015; 17 pages.
Office Action for U.S. Appl. No. 13/456,682 dated Dec. 17, 2014; 15 pages.
Notice of Allowance and Fees Due with Notice of Allowability for U.S. Appl. No. 14/189,772 dated Jun. 24, 2016; 7 pages.
Amendment and Response for U.S. Appl. No. 14/189,772, filed May 17, 2016; 6 pages.
Office Action for U.S. Appl. No. 14/189,772 dated May 3, 2016; 8 pages.
Supplemental Amendment for U.S. Appl. No. 14/189,772, filed Mar. 17, 2016; 14 pages.
Amendment for U.S. Appl. No. 14/189,772, filed Jan. 22, 2016; 20 pages.
Amendment and Response for U.S. Appl. No. 14/189,772, filed Jun. 27, 2015; 20 pages.
Office Action issued for U.S. Appl. No. 14/189,772 dated Apr. 27, 2015; 20 pages.
Notice of Allowance and Fee Due with Notice of Allowability for U.S. Appl. No. 15/005,116 dated Aug. 10, 2016; 7 pages.
Amendment and Response for U.S. Appl. No. 15/005,116, filed Jul. 18, 2016, with Terminal Disclaimer; 4 pages.
Office Action issued for U.S. Appl. No. 15/005,116 dated Jul. 13, 2016; 11 pages.
Office Action issued for U.S. Appl. No. 15/251,902 dated Oct. 3, 2018; 51 pages.
Response for U.S. Appl. No. 15/251,902, filed Jan. 3, 2019, with 2 Terminal Disclaimers; 3 pages.
Notice of Allowance and Fee Due with Notice of Allowability for U.S. Appl. No. 15/251,902 dated Feb. 19, 2019; 20 pages.

\* cited by examiner

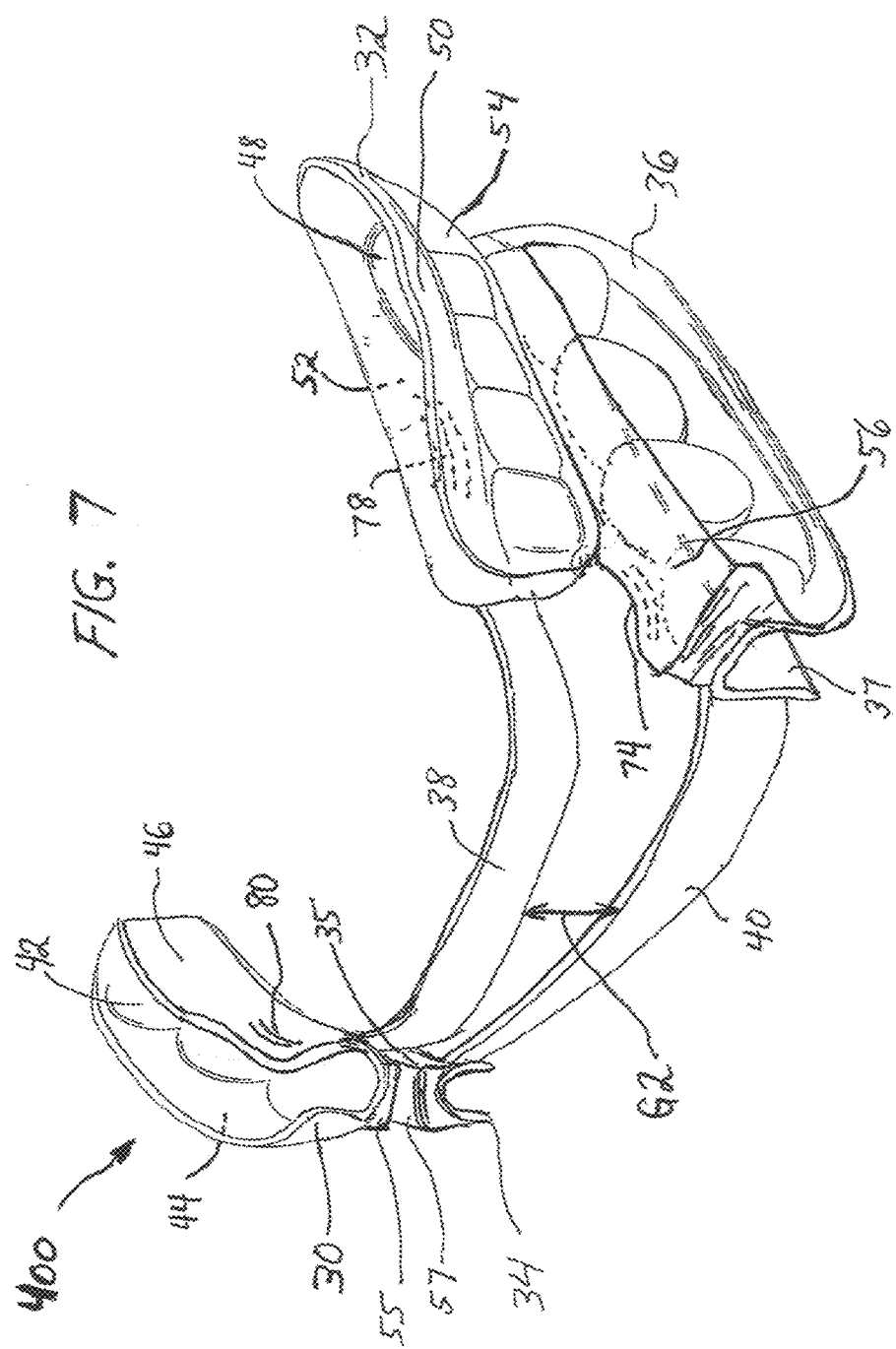

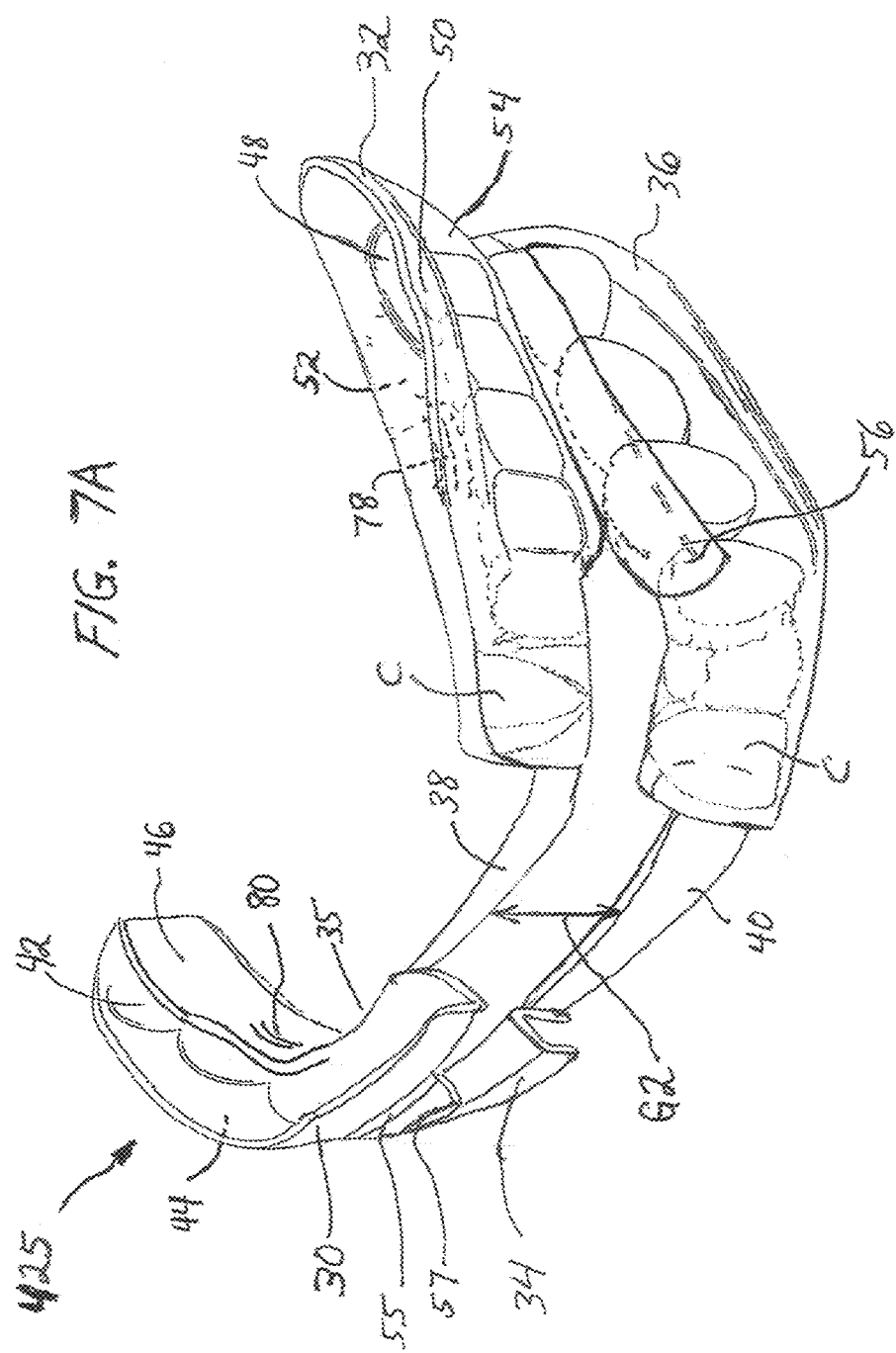

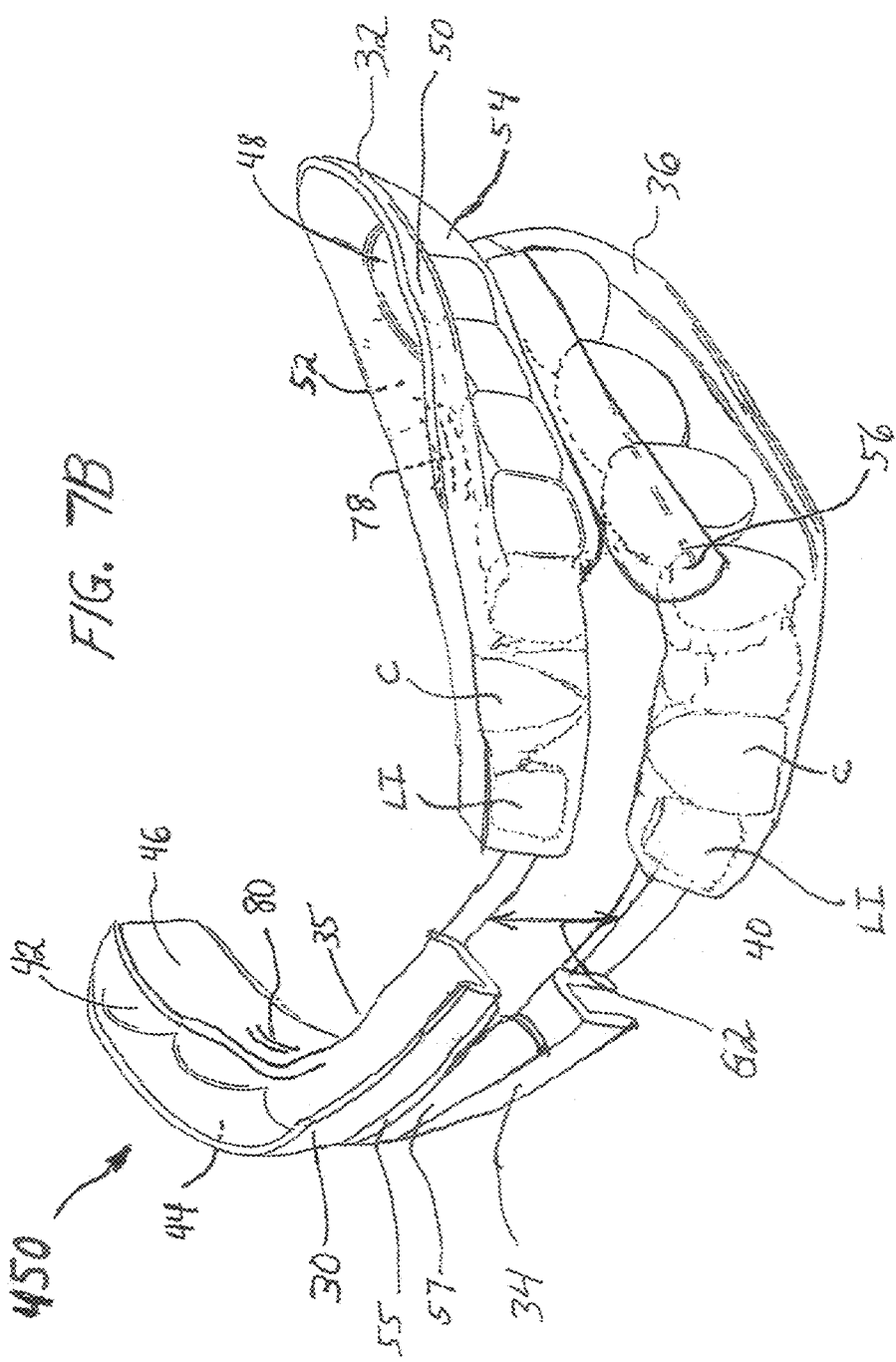

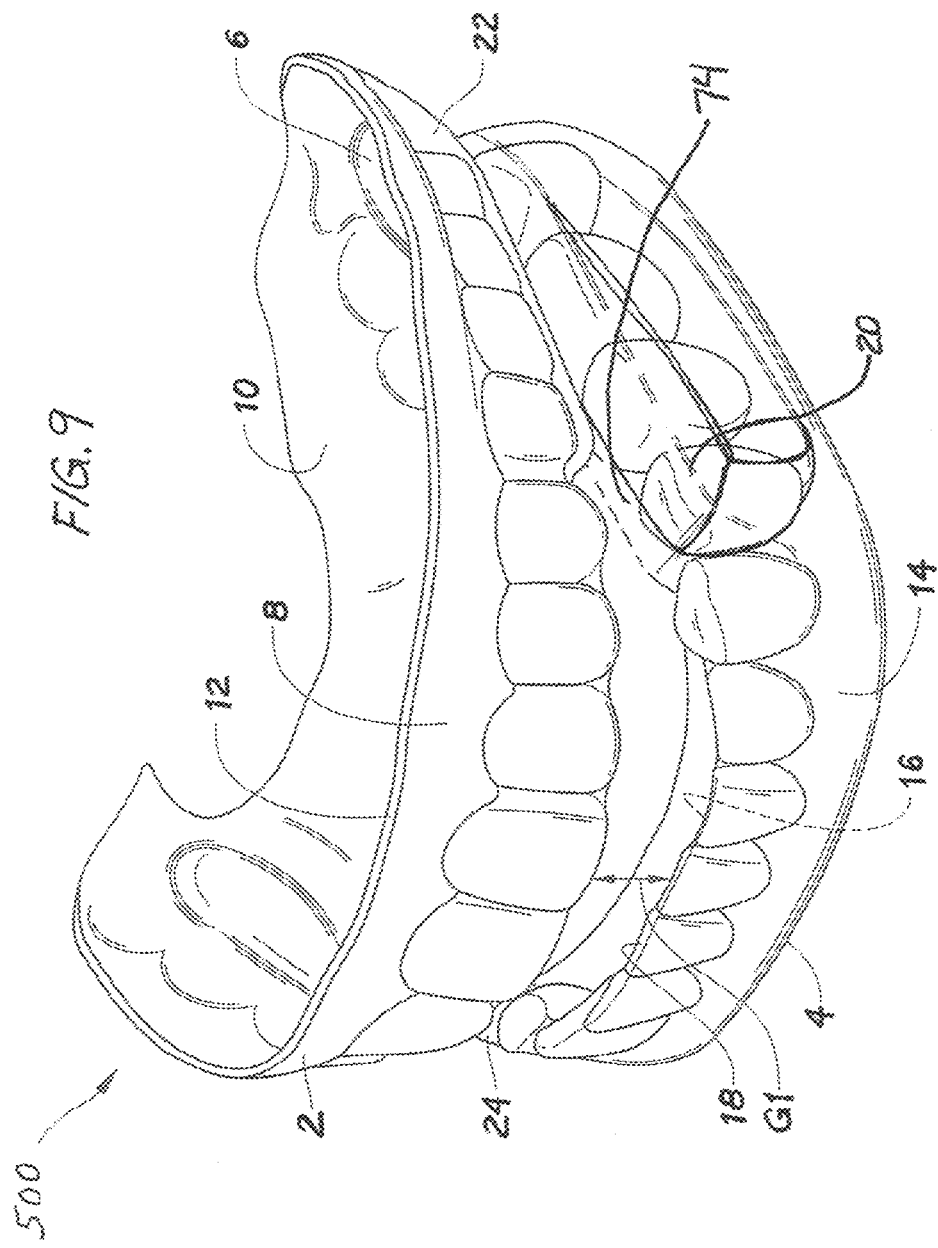

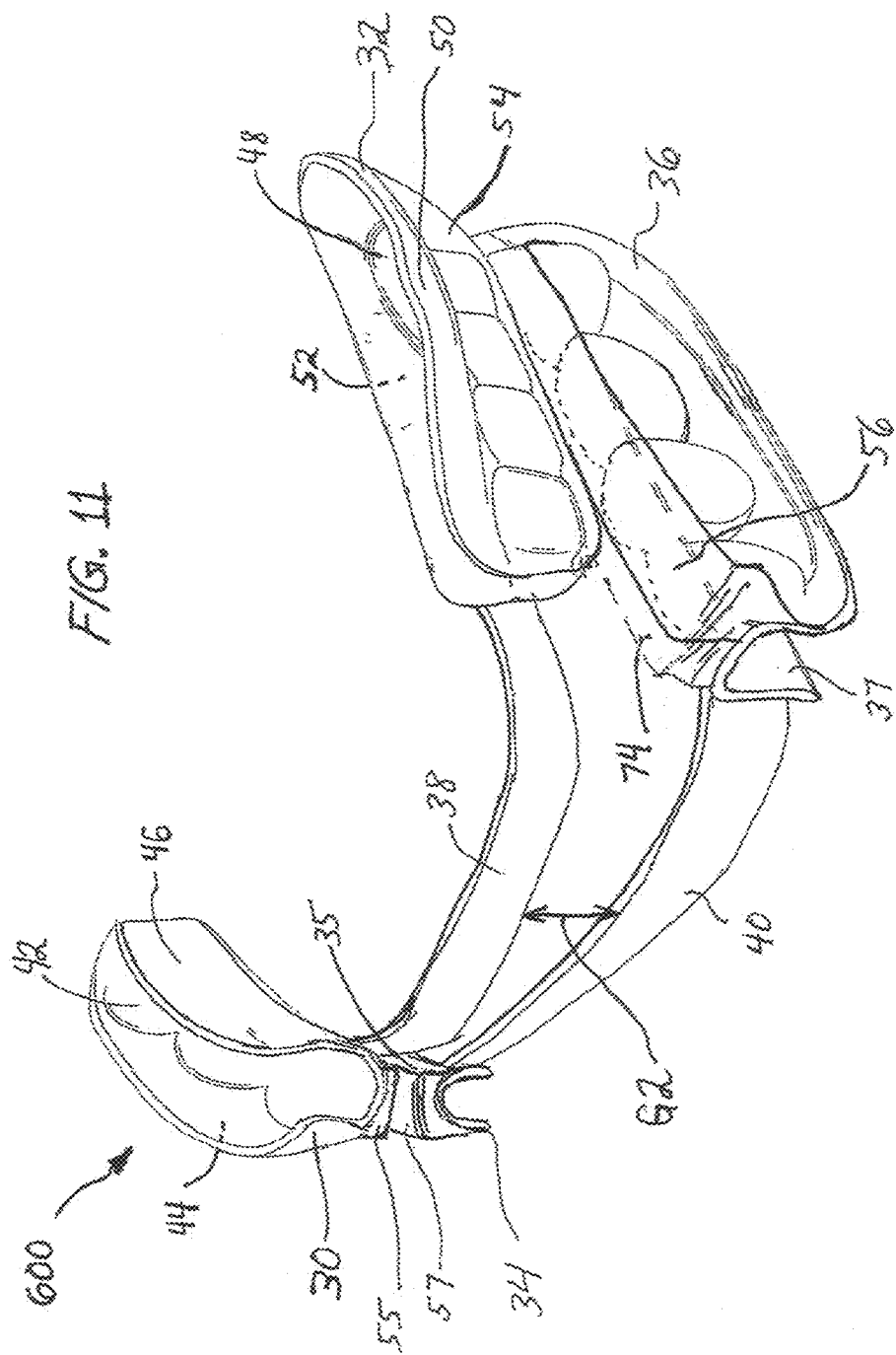

ORAL DEVICES

CROSS-REFERENCE TO RELATED APPLICATIONS

This application is entitled to and claims the benefit of earlier filed provisional application No. 62/869,528, filed Jul. 1, 2019, under 35 U.S.C. § 119(e), which earlier filed provisional application is incorporated by reference herein in its entirety. This application may be related to U.S. application Ser. No. 14/852,768, filed Sep. 14, 2015, now U.S. Pat. No. 9,439,802, which was a continuation of U.S. application Ser. No. 13/456,682, filed Apr. 26, 2012, now U.S. Pat. No. 9,144,512; U.S. application Ser. No. 15/251, 902, filed Aug. 30, 2016, now U.S. Pat. No. 10,299,957, which was a also a continuation of U.S. application Ser. No. 13/456,682, filed Apr. 26, 2012, now U.S. Pat. No. 9,144, 512; U.S. application Ser. No. 14/189,772, filed Feb. 25, 2014, now U.S. Pat. No. 9,408,743, which was a continuation-in-part of U.S. application Ser. No. 13/456,682, filed Apr. 26, 2012, now U.S. Pat. No. 9,144,512; and U.S. application Ser. No. 15/005,116, filed Jan. 25, 2016, now U.S. Pat. No. 9,445,938, which was a continuation of U.S. application Ser. No. 14/189,772, filed Feb. 25, 2014, now U.S. Pat. No. 9,408,743, all of which are incorporated herein by reference in their entirety.

BACKGROUND INFORMATION

Technical Field

The present disclosure relates to oral devices for reducing or eliminating snoring and/or improving sleep quality even if the user experiences little or no reduction in snoring.

Background Art

My previous patents, mentioned above, focused mainly on OSA, or obstructive sleep apnea, although in truth my patented devices may be used for a variety of purposes where a mouth piece may be beneficial, including sports mouth guards and reduction in snoring. The present application focuses mainly on reduction of snoring and/or improving sleep quality even if the user experiences little or no reduction in snoring.

There are of course many known oral devices that claim to reduce or eliminate snoring. As I explained in my previous patents, these oral devices are sometimes referred to as mandibular splints. Pharmaceuticals comprise another category. The present disclosure involves the oral device or mandibular splint category.

It has just recently come to my attention that when wearing my oral device, if the tongue were allowed even a small amount of extra room in the mouth, significant reduction in snoring could be achieved. US20160135922 discloses "a universal device to be inserted in the mouth, which would also be adapted to re-educate the tongue position", however, the document seems to teach re-education of the teeth, not the tongue. Regarding shaping of surfaces, the document discloses that for a better ergonomics of the device and its better positioning in the mouth, the first interocclusal surface and the second interocclusal surface have appropriate respective shapings on the side facing the center of the mouth. The device can thus assume an oblong shape or similar to a horseshoe with the ring that surrounds the soft parts of the tongue and the horizontal planes, the shields, and the front band that embrace other soft tissue and the teeth, in order to perform the stabilization function and allow the re-education and the positional disengagement of the teeth. However, this patent does not disclose an oral device employing aligning surfaces on the lower tray for the purpose of aligning the lower jaw as the user relaxes. The shaped surfaces in the above patent are used to "re-educate the tongue position." U.S. Pat. No. 6,634,353 discloses a method of treating apnea in a patient having sleep apnea and a malocclusion between the upper and lower mandibles. However, this patent does not disclose an oral device employing aligning surfaces (not points) on the lower tray for the purpose of aligning the lower jaw as the user relaxes. The method disclosed is for curing malocclusion (lack of occlusion) and includes measuring steps and determining a centering position of the malocclusion and includes use of rubber bands or other biasing means. U.S. Pat. No. 9,585, 785 (Hofmann), discloses an "occlusion splint arrangement", featuring "fins" having centering pins and recesses, as seen in the figures of the patent. However, this patent does not disclose an oral device employing aligning surfaces, rather it teaches use of pins and recesses on the lower tray for the purpose of aligning the lower jaw as the user relaxes.

Many of the known oral devices meant to reduce snoring are uncomfortable and/or complicated, leading to reduced use, or non-use. Furthermore, their use in humans may reduce speaking substantially, or at least the ability to speak understandably. In my previous patents I described upper and lower trays that fit over the inside and outside surfaces of a user's upper and lower dentition, respectively, and certain embodiments include left and right ramps designed to move the lower mandible (lower jaw) downward as it moves backward toward a users throat. While I have found devices of this nature to be effective in reducing or eliminating my sleep apnea and snoring, and met a long felt and unmet need for such an oral device, apparatus or kit, and methods of using these, to efficiently, safely and comfortably reduce or prevent OSA, snoring, and/or nasal drainage, the use of trays covering the front teeth may not be optimal for all users, and the shape of the ramps may be complicated to manufacture. In particular, some of the ramps disclosed in my previous patents may have complicated mating surfaces, which must mate smoothly to be comfortable and effective for users. Devices marketed by others may include engagement features to engage posterior portions of upper and lower trays to stabilize the upper and lower trays relative to one another, and thereby stabilize the subject's upper and lower jaw relative to one another. In my personal experience, such stabilization in devices designed to prevent snoring and/or sleep apnea are highly undesirable, as they lead to jaw soreness and stiffness, and ultimately non-use of the device.

I have found that it may also be beneficial to reduce friction of the mating surfaces of my devices. Many inventions in the dental area disclose the use of "patterned surface" features, but none that I am aware of disclose patterned surfaces to reduce friction. U.S. Pat. Nos. 4,479, 527 and 4,531,566 disclose use of a patterned surface made by a mesh or screen such as woven polymer made of polyethylene fibers. The patterned surface is used to increase bonding, as when making a dental bridge, not to reduce friction. WO2014087412A1 discloses a hydrothermal alkaline, non-toxic process for making metallic implants for better bio-integration of implants.

I have also found that it may be beneficial to users to have an oral device shaped such that when a user's lower jaw relaxes, the lower tray tends to center itself, and thereby the lower jaw.

In light of the above problems, and no apparent solutions available to oral device users, I have designed several oral devices that reduce possible alignment problems with my previous device and devices of like nature, which are easier and less costly to manufacture, and which provide added room for the tongue to relax.

SUMMARY

In accordance with the present disclosure, oral devices, apparatus and kits are presented, as well as methods of using same, which reduce or overcome snoring, and which may benefit those suffering from obstructive sleep apnea, and other loss of sleep issues, and/or nasal drainage.

A first aspect of the disclosure is an oral device or apparatus (the words "apparatus" and "oral device" are used interchangeably herein) comprising:

- an upper generally arched-shaped member that is configured to fit adjacent at least a portion of interior and exterior surfaces of a user's upper dentition, the upper generally arched-shaped member comprising a first moldable or printable polymeric material;
- a lower generally arched-shaped member that is configured to fit adjacent at least a portion of interior and exterior surfaces of a user's lower dentition, the lower generally arch-shaped member comprising a second moldable or printable polymeric material, the first and the second moldable or printable polymeric materials are the same or different;
- the lower generally arch-shaped member comprising a lower right molar and pre-molar extension and a lower left molar and pre-molar extension, each comprising a moldable or printable polymeric material, the lower right and the lower left molar and pre-molar extensions formed integrally with and projecting generally perpendicularly away from the lower generally arch-shaped member and generally toward the upper generally arch-shaped member;
- the upper generally arch-shaped member comprising an upper right molar and pre-molar extension and an upper left molar and pre-molar extension, each comprising a moldable or printable polymeric material, the upper right and upper left molar and pre-molar extensions formed integrally with and projecting generally perpendicularly away from the upper generally arch-shaped member and generally toward the lower generally arch-shaped member;
- so that when the user bites or clenches, the upper right molar and pre-molar extension impinges on the lower right molar and pre-molar extension, and the upper left molar and pre-molar extension impinges on the lower left molar and pre-molar extension;
- the upper and lower generally arch-shaped members having an anterior shape to form a gap sufficient for at least a portion of the user's tongue to extend forward into the gap without being impeded in forward movement by the apparatus;
- the lower right molar and pre-molar extension, lower left molar and pre-molar extension, upper right molar and pre-molar extension, and upper left molar and pre-molar extension configured such that, when the apparatus is in the user's mouth, the molar extensions create a tendency to keep the user's airway open by maintaining the gap;
- at least one of the lower right molar and pre-molar extension, the lower left molar and pre-molar extension, the upper right molar and pre-molar extension, and the upper left molar and pre-molar extension having a patterned surface where the upper right molar and pre-molar extension impinges on the lower right molar and pre-molar extension, and the upper left molar and pre-molar extension impinges on the lower left molar and pre-molar extension.

A second aspect of the disclosure is a method of making an oral device of the first aspect, the method comprising:

- scanning a user's upper and lower dentitions and mouth cavity employing a laser scanning or CT scanning device to produce a pointcloud image thereof;
- uploading the pointcloud image to a computer having one or more dental design software loaded thereon and producing a software version of the oral device from the pointcloud image;
- uploading the software version of the oral device to a 3D printer;
- 3D printing the upper generally arched-shaped member of the first aspect;
- 3D printing the lower generally arched-shaped member of the first aspect;
- wherein the 3D printing of the lower right molar and pre-molar extension, the lower left molar and pre-molar extension, the upper right molar and pre-molar extension, and the upper left molar and pre-molar extension comprises 3D printing the patterned surface or surfaces.

A third aspect of the disclosure is an oral device comprising upper and lower generally arched-shaped members as described in the first aspect, except that rather than (or in addition to) having patterned surfaces,

- the lower right molar and pre-molar extension, lower left molar and pre-molar extension, upper right molar and pre-molar extension, and upper left molar and pre-molar extension each configured with arcuate interior surfaces such that, when the apparatus is in the user's mouth, the arcuate interior surfaces create left and right sub-chambers allowing more room for the user's tongue.

A fourth aspect of the disclosure is a method of making an oral device of the third aspect, comprising:

- scanning a user's upper and lower dentitions and mouth cavity employing a laser scanning or CT scanning device to produce a pointcloud image thereof;
- uploading the pointcloud image to a computer having one or more dental design software loaded thereon and producing a software version of the oral device from the pointcloud image;
- uploading the software version of the oral device to a 3D printer; and
- 3D printing the upper and lower generally arched-shaped members (as described in the first aspect) with a composition comprising a first moldable or printable polymeric material (the upper and lower members made comprise the same or different moldable or printable polymeric materials);
- wherein the 3D printing of the lower generally arch-shaped member and the upper generally arch-shaped member comprises 3D printing a shaped interior member having arcuate interior surfaces such that, when the apparatus is in the user's mouth, the arcuate interior surfaces create left and right sub-chambers allowing more room for the user's tongue.

A fifth aspect of the invention is an oral device comprising upper and lower generally arched-shaped members as described in the first aspect, except that rather than (or in addition to) having patterned surfaces, the lower and upper right molar and pre-molar extensions are shaped to form a right-side lateral sub-chamber for tongue, and the lower and upper left molar and pre-molar extensions are shaped to form a left-side lateral sub-chamber for the tongue, the left and right sub-chambers sufficient for at least left and right sub-portions of the user's tongue to extend generally laterally into the left and right sub-chambers when the user's tongue relaxes.

A sixth aspect of the disclosure is a method of making of making an oral device of the fifth aspect, comprising:

scanning a user's upper and lower dentitions and mouth cavity employing a laser scanning or CT scanning device to produce a pointcloud image thereof;

uploading the pointcloud image to a computer having one or more dental design software loaded thereon and producing a software version of the oral device from the pointcloud image;

uploading the software version of the oral device to a 3D printer; and 3D printing the upper and lower generally arched-shaped members (as described in the first aspect) with a composition comprising a first moldable or printable polymeric material (the upper and lower members made comprise the same or different moldable polymeric materials);

wherein the 3D printing of the lower generally arch-shaped member and the upper generally arch-shaped member comprises 3D printing the shapes to form the left-side and the right-side lateral sub-chambers, the left-side and right-side sub-chambers sufficient for at least left and right sub-portions of the user's tongue to extend generally laterally into the left-side and right-side sub-chambers when the user's tongue relaxes.

A seventh aspect of the invention is an oral device comprising upper and lower generally arched-shaped members as described in the first aspect, except that rather than (or in addition to) having patterned surfaces, the first and second generally arch-shaped members each having a second tier of pre-molars and molars attached to or formed integrally with the substantially flat first molar and pre-molar extensions so that when the user bites or clenches, the second tier of molar and pre-molar extensions impinge on the user's lower or upper dentition, the first and second generally arch-shaped members linked together by a palatal band.

In certain embodiments the lower and the upper generally arch-shaped members are "full members", meaning that the upper generally arch-shaped member covers and fits over a user's entire upper dentition, and the lower generally arch-shaped member fits over a user's entire lower dentition. Stated differently, "full members" means that every cross-section of the upper generally arch-shaped member is U-shaped, while every cross-section of the lower generally arch-shaped members is an inverted U-shape. In other embodiments, the lower and the upper generally arch-shaped members are both lacking frontal vestibular bands in the areas in front of the incisors and the canines, while one upper palatal band connects left and right pre-molar and molar trays adjacent and behind the upper incisors and canines, and a similar lower palatal band connects left and right pre-molar and molar trays adjacent and behind the lower incisors and canines. In other embodiments, the lower and the upper generally arch-shaped members both cover the molars, premolars, canines, and lateral incisors but not the central incisors, effectively leaving four teeth (two maxillary central incisors and two mandibular central incisors) uncovered by either of the generally arch-shaped members, but having two palatal bands, one connecting the upper left and upper right generally arch-shaped members, and the other connecting the lower left and lower right generally arch-shaped members, but lacking any vestibular bands. In other embodiments, the lower and the upper generally arch-shaped members both cover the molars, premolars, and canines, but not the lateral or central incisors, effectively leaving eight teeth (four maxillary incisors and four mandibular incisors) uncovered by either of the generally arch-shaped members, but having two palatal bands, one connecting the upper left and upper right generally arch-shaped members, and the other connecting the lower left and lower right generally arch-shaped members, but lacking any vestibular bands. In certain embodiments the patterned surface may be selected from the group consisting of fingerprint patterns, chevron-patterns, spiral patterns, dot patterns, and random, computer-generated patterns.

In certain embodiments the moldable or printable biocompatible polymeric material may be selected from the group consisting of synthetic and natural materials. As used herein "moldable" includes polymeric materials that nay be shaped by heat and molding. As used herein "printable" is intended to include additive manufacturing processes as described herein, and wherein either the end polymer itself is printable, or its precursor resins are printable and that may be later cured or otherwise solidified, for example by light having wavelengths in the UV light ranges or IR light (heat) ranges or other wavelengths, depending on the resin. In certain embodiments the moldable or printable biocompatible polymeric material may be selected from the group consisting of polyurethanes, polysulfones, polycarboxylates, perfluorinated polymers, polyacrylics, polyvinyls, polyvinyl alcohols, silicones, polyolefins, and blends and copolymers thereof. In certain embodiments the moldable or printable biocompatible polymeric material may be selected from a durable fade-resistant acrylic that retains its shape and color for at least four years, and a very pliable, soft, custom-injected silicone.

In certain embodiments, the upper and lower generally arched-shaped members each consist essentially of an identical moldable or printable, biocompatible polymeric material. Any of the oral devices or apparatus described herein may be part of a kit comprising one or both upper and lower generally arch-shaped members substantially as described herein, in certain embodiments packaged in a carrying case.

Further aspects and advantages of apparatus and methods of the present disclosure will become apparent by reviewing the detailed description that follows.

BRIEF DESCRIPTION OF THE DRAWINGS

FIGS. 1, 5, and 9 are perspective schematic illustrative views of three "full member" apparatus or kit embodiments within the present disclosure;

FIGS. 3, 7, 7A, 7B, 11, 16, and 17 are perspective schematic illustrative views of six "partial member" apparatus or kit embodiments within the present disclosure, with the embodiments illustrated in FIGS. 7, 7A, 7B, 16, and 17 having some features illustrated in phantom;

FIGS. 16 and 17 are schematic perspective and flipped perspective illustrative views, respectively, of another oral device embodiment of the present disclosure.

Figure 1:
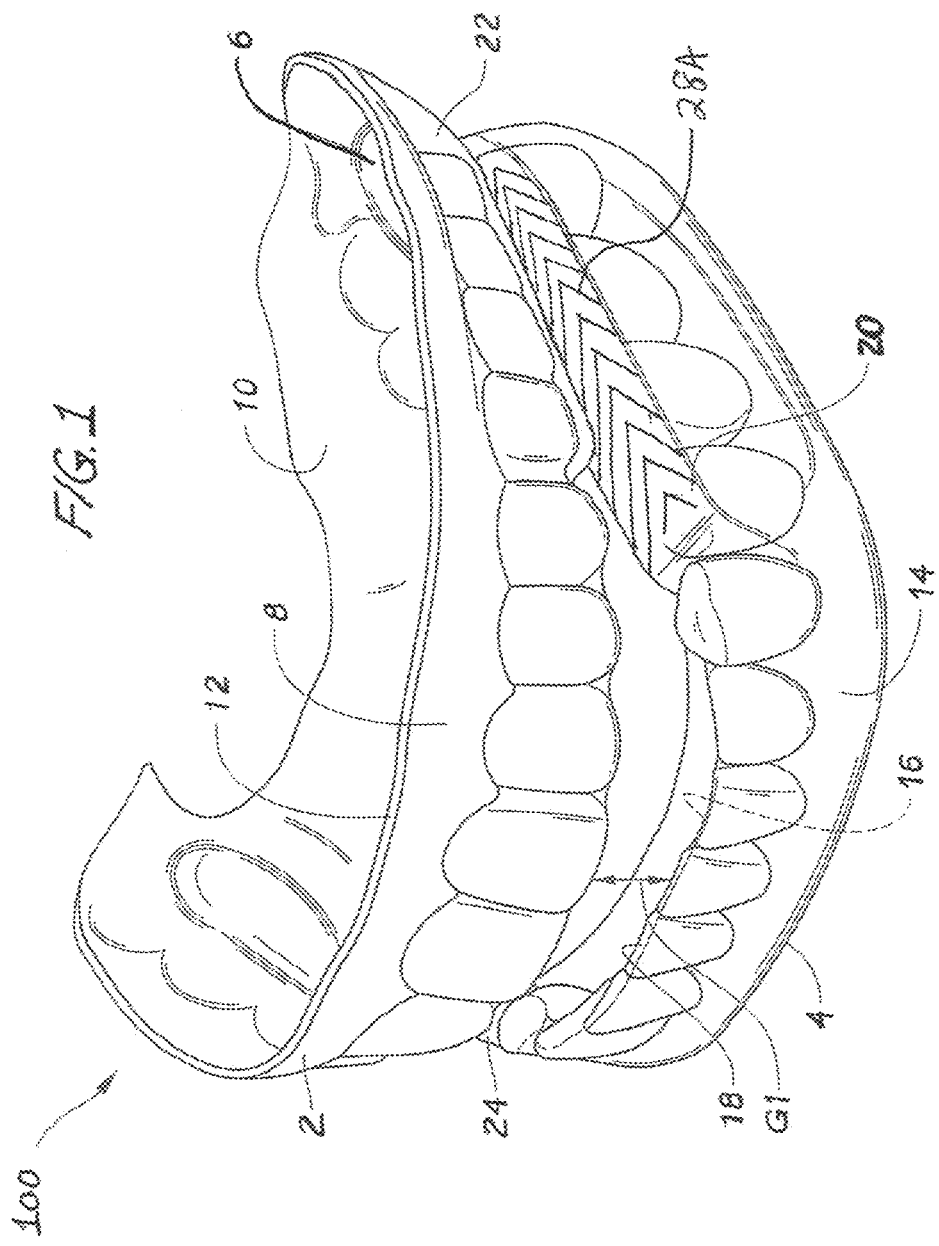

It is to be noted, however, that the appended drawings are not to scale and illustrate only typical embodiments of this disclosure and are therefore not to be considered limiting of its scope, for the apparatus, kits, and methods of the disclosure may admit to other equally effective embodiments. Identical reference numerals are used throughout the several views for like or similar elements.

DETAILED DESCRIPTION

In the following description, numerous details are set forth to provide an understanding of the disclosed oral devices, kits and methods of their use. However, it will be understood by those skilled in the art that the oral devices, kits, and methods covered by the claims may be practiced without these details and that numerous variations or modifications from the specifically described embodiments may be possible and are deemed within the claims. For example, wherever the term "comprising" is used, embodiments and/or components where "consisting essentially of" and "consisting of" are also explicitly disclosed herein and are part of this disclosure. An example of "consisting essentially of" may be with respect to the composition of a generally arch-shaped member: a generally arch-shaped member consisting essentially of a biocompatible polymer means there may be a minor portions or trace amounts of organic and/or inorganic chemical species, such monomers and other polymer precursors, noble metals such as platinum, and the like. An example of "consisting of" may be an oral device made up of components that are one or more biocompatible polymers and no or substantially no other chemical species. Another example of "consisting essentially of" may be with respect to a particular patterned surface that consists essentially of a non-random dot pattern, meaning that a minor portion, perhaps up to 10, or up to 5, or up to 4, or up to 3, or up to 2, or up to 1 wt. percent may be randomly placed. An example of oral devices using the transition phrase "consisting of" includes those where a device has only molar and premolar trays, with one band connecting the upper left and right trays, and a second band connecting the lower left and right trays, molar and premolar extensions on each tray, and patterned surfaces on each extension. The term "comprising" and derivatives thereof is not intended to exclude the presence of any additional component, step or procedure, whether or not the same is disclosed herein. In order to avoid any doubt, all compositions, apparatus, systems, and methods claimed herein through use of the term "comprising" may include any additional component, step, or procedure unless stated to the contrary. In contrast, the term, "consisting essentially of" excludes from the scope of any succeeding recitation any other component, step or procedure, excepting those that are not essential to operability. The term "consisting of" excludes any component, step or procedure not specifically delineated or listed. The term "or", unless stated otherwise, refers to the listed members individually as well as in any combination. Unless stated to the contrary, implicit from the context, or customary in the art, all parts and percentages are based on weight and all test methods are current as of the filing date hereof. The acronym "ASTM" means ASTM International, 100 Barr Harbor Drive, PO Box C700, West Conshohocken, PA, 19428-2959 USA. All numbers, including degree angles, disclosed herein are approximate values, regardless whether the word "about" or "approximate" is used in connection therewith. They may vary by 1%, 2%, 5%, and sometimes, 10 to 20%. Whenever a numerical range with a lower limit, RL and an upper limit, RU, is disclosed, any number falling within the range is specifically disclosed. In particular, the following numbers within the range are specifically disclosed: R=RL+k*(RU−RL), wherein k is a variable ranging from 1% to 100% with a 1% increment, i.e., k is 1%, 2%, 3%, 4%, 5%, . . . , 50%, 51%, 52%, . . . , 95%, 96%, 97%, 98%, 99%, or 100%. Moreover, any numerical range defined by two R numbers as defined in the above is also specifically disclosed.

All percentages herein are based on weight unless otherwise specified. All U.S. patent applications and U.S. Patents referenced herein, and their priority documents, are hereby explicitly incorporated herein by reference. In the event definitions of terms in the referenced patents and applications conflict with how those terms are defined in the present application, the definitions for those terms that are provided in the present application shall be deemed controlling.

As used herein the phrase "generally arched-shaped" means the shape of a member resembles an arch in the same way that the upper and lower teeth of a user resemble arches. The phrase "adjacent at least a portion of interior and exterior surfaces", as that term is used herein when referring to the "upper and lower generally arched-shaped members configured to fit adjacent at least a portion of interior and exterior surfaces of a user's upper and lower dentitions", means that these members are adjacent to and touching at least one surface of the upper or lower teeth concerned, but some "looseness" is allowed, so that the members may move away from the teeth slightly, for example if the material of the member stretches or deforms, such as during insertion into or removal from the mouth. In certain embodiments "adjacent" in this context means a separation of from about 0.05 to about 0.5 mm, or from about 0.1 to about 0.3 mm. The term "molar extension" is meant to convey general location, and does not mean that the extensions are always precisely covering all molars and premolars in those locations; in other words, a they are meant to be relative terms, such as front and back, upper and lower, and the like, are relative terms. "Canines" or "canine" location is generally between lower (mandibular) premolars and lower incisors, and between upper premolars and upper incisors; "molars" is used herein to include premolars. As used herein the term "user" means a human or other mammal that employs an apparatus of this disclosure in its mouth. The term "subject" may also be used and is considered interchangeable with the term "user." As used herein the term "patterned surface" means any random or non-random collection of surface features that would tend to reduce friction when the surface is drawn across another surface.

The present disclosure relates generally to apparatus, kits, and methods for reducing or eliminating snoring, although they may also be beneficial for reducing or eliminating sleep disorders and other disorders, such as obstructive sleep apnea (OSA) and/or nasal drainage. A particular use for apparatus and kits of this disclosure is for humans, but they may also be used for other mammals. Certain embodiments may also be used as athletic mouth guards for upper, lower, or both dentitions.

In certain embodiments, the gap (denoted G1 in the various figures) may have a distance ranging from about 1 to about 20 mm, or from about 5 to about 15 mm. In certain embodiments, patterned surface features may have a height ranging from about 0.5 mm up to about 3.0 mm, or from about 0.5 to about 2.5 mm, or up to about 2.0 mm, or up to about 1.5 mm, or up to about 1.0 mm. The surface features on one patterned surface may, but are not required to have the same height, and may, but are not required to have the same shape.

The lateral length of the upper and lower molar extensions, i.e., the distance from the posterior terminus to the anterior terminus of a given molar extension, may be 10 mm or more, or may range from 10 to about 50 mm or from about 12 to about 24 mm. In certain embodiments, the total distance D1 (as more fully described in reference to FIG. 6A) between upper and lower molars created by the combined thickness of upper and lower trays and molar extensions may range from about 5 to about 10 mm, or from about 6 mm to about 9 mm, or from about 6.5 mm to about 7.5 mm, while the distance D2 designates the thickness of only the upper tray and molar extension, and may range from about 4 to about 9 mm, or from about 5 mm to about 8 mm, or from about 5.5 mm to about 7.5 mm, with the proviso that D1>D2. Stated differently, the ratio D2/D1 may range from about 4/10 to about 9/10, or from about 5/10 to about 8/10, or from about 5/7 to about 6.8/7.

In certain embodiments the upper and lower members each may comprise a moldable material selected from the group consisting of synthetic and natural materials. Synthetic materials may be selected from the group consisting of polymeric materials, as further discussed herein. In certain apparatus the arch-shaped members, molar extensions, patterned surfaces, and shaped members may comprise the same or different polymeric materials.

Figure 2:
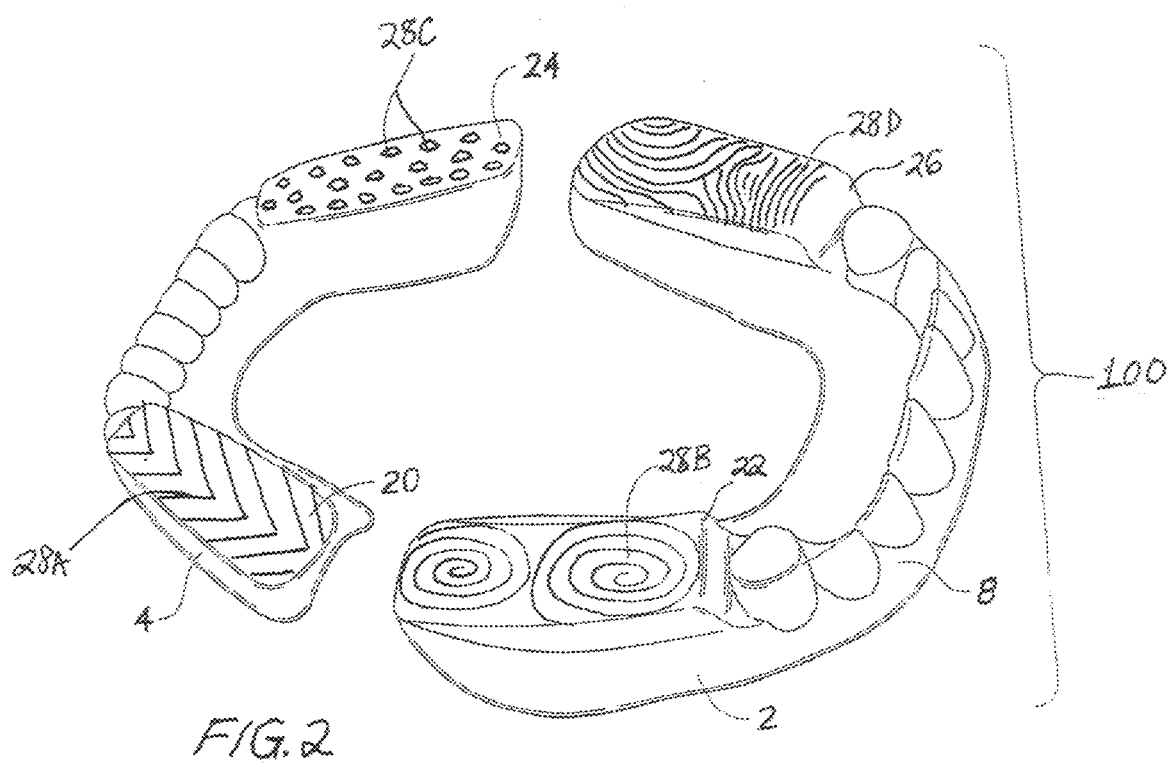
FIGS. 2, 6, and 10 are exploded schematic illustrative views of the three embodiments illustrated in FIGS. 1, 5, and 9, respectively, with FIGS. 6A and 10A being cross-sectional views viewed frontally.

Referring now to FIGS. 1 and 2, FIG. 1 illustrates schematically a perspective view of one apparatus 100 in accordance with the disclosure. Apparatus embodiment 100 includes a full upper generally arch-shaped member 2 and a full lower generally arch-shaped member 4. Upper generally arch-shaped member 2 includes an exterior wall 8 and an interior wall 10, custom-shaped for the user's upper dentition, and which together define a trough 6 for friction fitting adjacent the upper dentition of a user. An upper connecting portion 12 connects exterior wall 8 and interior wall 10. Connecting portion 12 may be rather thin or pointed in the area of the front teeth, and rather flat or planar in the area of the back molar teeth. Similarly, lower generally arch-shaped member 4 includes an exterior wall 14, and an interior wall 16. A lower connecting portion 18 connects walls 14 and 16, and as with upper connecting portion 12, lower connecting portion 18 may be rather thin or pointed near the front teeth of the user, and rather flat or planar near the lower molars of the user.

Embodiment 100 includes a lower left, generally arch-shaped molar and premolar extension 20 and an upper left molar and premolar extension 22, each extending generally perpendicularly away from their respective members. FIG. 2 illustrates schematically upper full generally arch-shaped member 2 in a 180 degree flip from its "in use" position to more clearly illustrate a lower right, generally arch-shaped molar and premolar extension 24 and an upper right molar and premolar extension 26. Full members 2 and 4, as well as molar extensions 20, 22, 24, and 26 may comprise the same moldable or printable polymeric material.

Molar extensions 20, 22, 24, and 26 may comprise, or consist essentially of, or consist of patterned surfaces (28A, 28B, 28C, and 28D) of the same moldable, biocompatible polymeric material formed integrally with their respective molar extensions, either by molding and shaping operations, or by 3D printing or other additive manufacturing methods. Pattern surfaces 28A, 28B, 28C, and 28D may be the same or different in certain embodiments. FIG. 2 simply illustrates four possible pattern surfaces. Patterned surface 28A is a chevron pattern; pattern 28B is a series of spirals; pattern 28C is a random pattern of dots; and pattern 28D is a fingerprint pattern. Upper full generally arch-shaped member 2 may comprise, or consist essentially of, or consist of upper left and upper right molar extensions (22, 26) of the same moldable, biocompatible polymeric material formed integrally therewith. Upper molar extensions 22, 26 project generally perpendicularly away from upper full generally arch-shaped member 2 and generally toward respective lower molar regions of member 4 in mating configuration. Patterned surfaces 28A, 28B, 28C, and 28D are configured such that when the user bites, upper right molar extension 26 impinges on lower right molar extension 24 only at the peaks of the patterned surfaces, thereby reducing friction as the user moves his or her mandible laterally, forwardly, or rearward.

Extensions 20, 22, 24, and 26 and patterned surfaces 28A, 28B, 28C, and 28D are selected and configured such that, when the apparatus is in a user's mouth, the lower dentition, lower full generally arched-shaped member 4, and mandible are not constrained in forward (anterior) movement, and allow lower full generally arch-shaped member 4, lower dentition and mandible to move with less friction when moved forward (anterior) away from the user's throat, tending to keep a user's throat airway open. Furthermore, upper and lower full generally arch-shaped members 2, 4, are configured to form a gap G1 sufficient for at least a portion of the user's tongue to extend forward into the gap without being impeded in forward movement by the apparatus, and without the tongue being constrained, pulled or grabbed in any way. During use, although movement of the lower jaw backwards is a natural movement during sleep, as this occurs, embodiment 100 will tend to allow the user to more easily move the mandible forward and keep the throat airway open, as well as by creating a gap between upper portion 2 and lower portion 4, near the front teeth, as indicated by double-headed arrow G1 in FIG. 1, and partially defined by space between anterior portions of upper and lower molar extensions 20, 22, 24, 26. This gap may be important in methods of reducing nasal drainage, perhaps more important than forward movement of the lower jaw.

Figure 3:
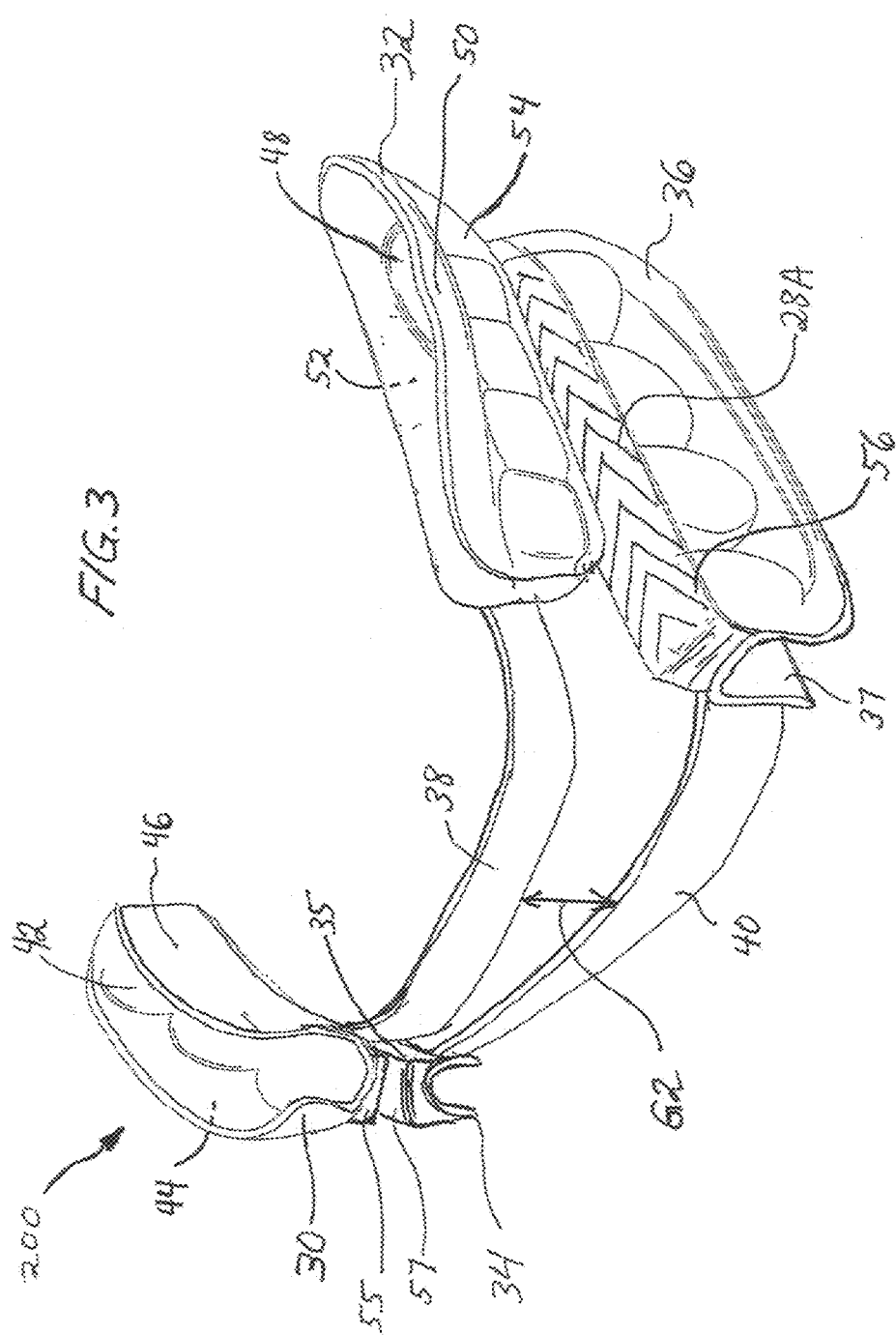
Figure 4:
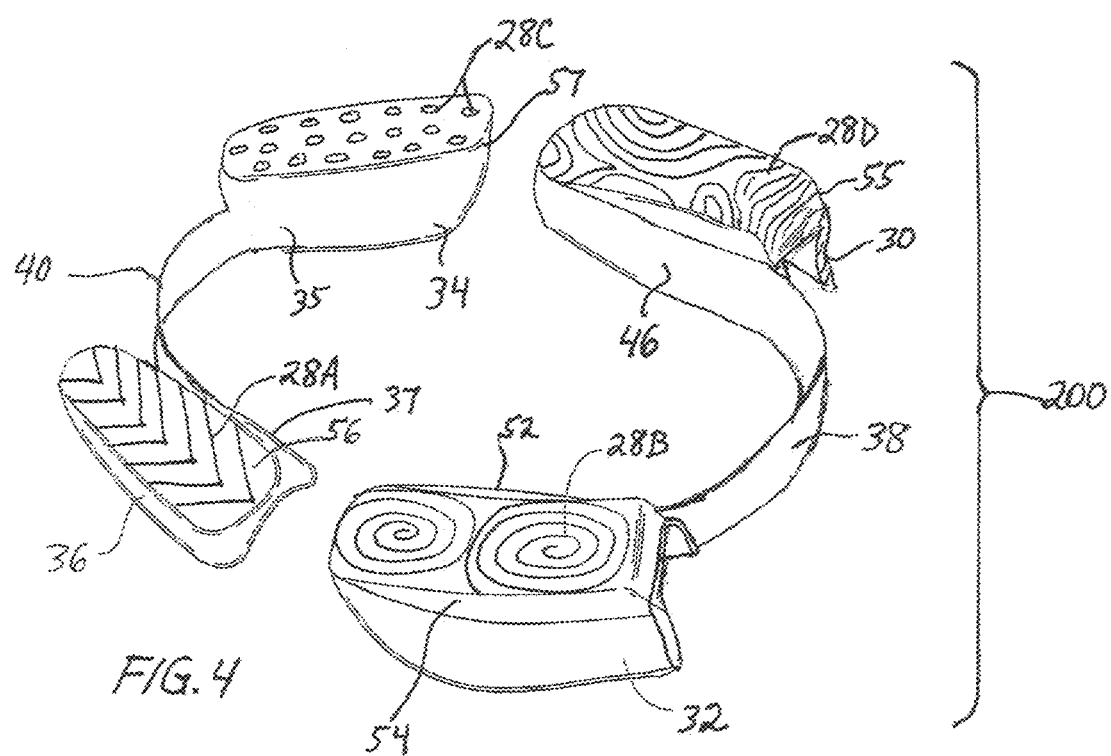
FIGS. 4, 8, and 12 are exploded schematic illustrative views of the three embodiments illustrated in FIGS. 3, 7, and 11, respectively, with FIGS. 8A and 12A being cross-sectional views viewed frontally.

FIG. 3 is a schematic perspective view of another apparatus or kit embodiment 200 within the present disclosure. As generally may be seen in FIG. 3, in this embodiment the oral device has an upper right molar tray 30, generally U-shaped in cross-section. Embodiment 200 further includes an upper left molar tray 32, a lower right molar tray 34, and a lower right molar tray 36, all generally U-shaped in cross-section. An upper palatal band 38 and a lower palatal band 40 are provided. Upper palatal band 38 connects upper right and upper left molar trays 30, 32, at interior walls 46, 52 of those upper trays, while lower palatal band 40 connects lower right and left molar trays 34, 36, at interior walls 35, 37. Upper right molar tray 30 includes an exterior wall 44, with walls 44, 46 forming the legs of a U-shaped trough 42. Upper left molar tray 32 has a similar U-shaped trough 48 with legs of the U defined by exterior wall 50 and interior wall 52. Embodiment further includes an upper left molar and premolar extension 54, an upper right molar and premolar extension 55, a lower left molar and premolar extension 56, and a lower right molar and premolar extension 57. Embodiment 200 will tend to keep a user's airway open by creating a gap between upper palatal band 38 and lower palatal band 40, each of which fit adjacent and behind their respective upper and lower incisors and canines, as indicated by double-headed arrow G2 in FIG. 3 through action of molar extensions 54, 55, 56, 57, and patterned surfaces 28A, 28B, 28C, 28D, substantially as in embodiment 100, but with less material required. In certain embodiments, palatal bands 38, 40 may be made to conform substantially to the rear surfaces of the user's upper and lower incisors and canines, whether by molding or by 3D printing. In certain embodiments palatal band 38 may be extended posterior along a portion of, or substantially all of the palate, as in the case of dental retainers, but this would be more costly in terms of materials. FIG. 4 is an exploded view of embodiment 200, illustrating that same or different pattern surfaces 28A-D may be employed.

Figure 5:
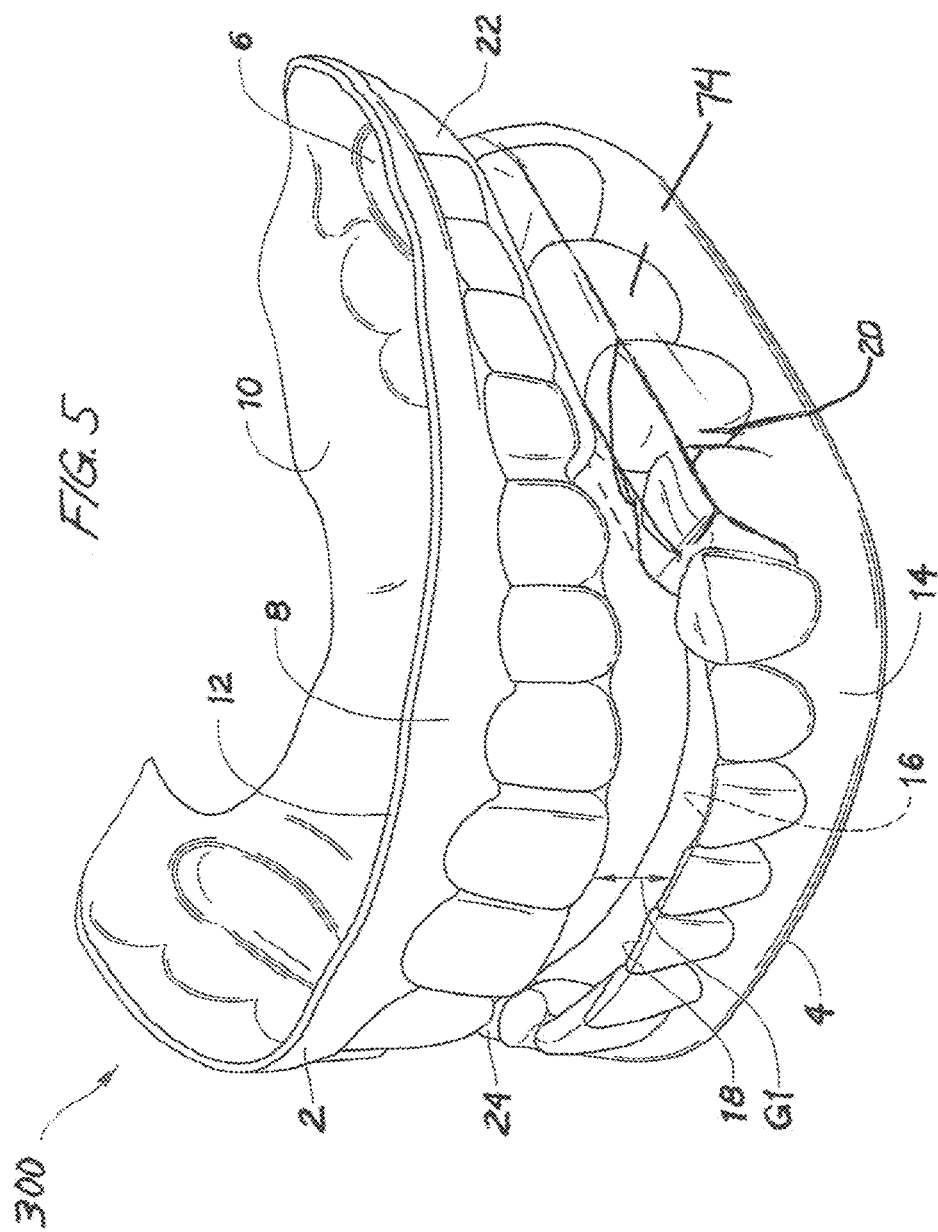
Figure 6:
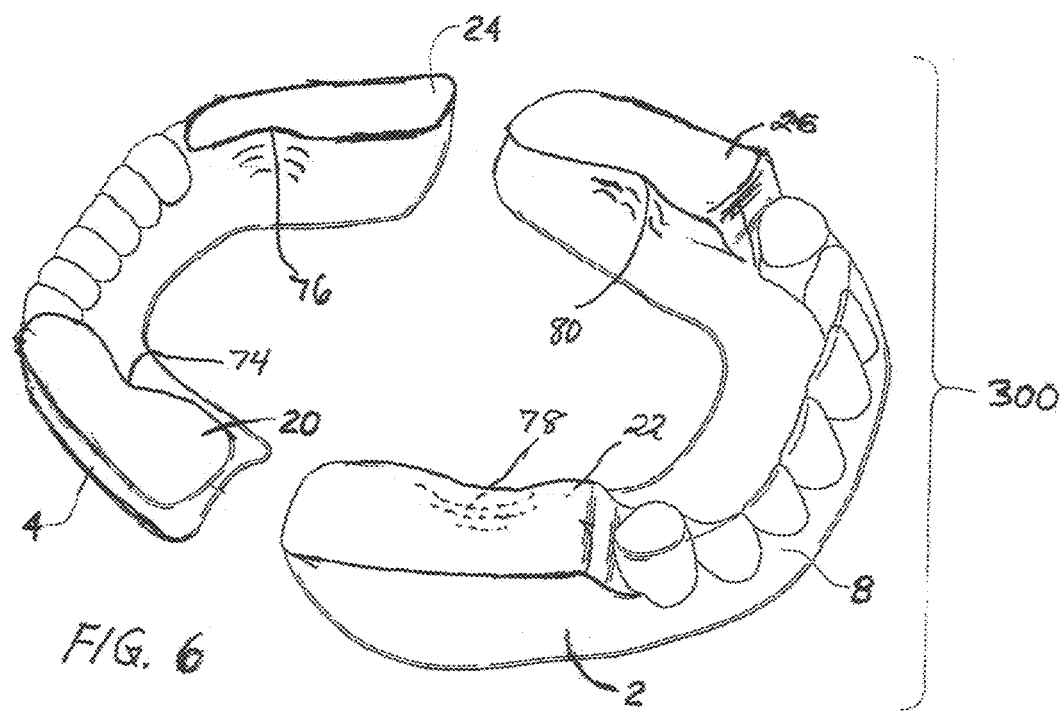
Figure 6A:
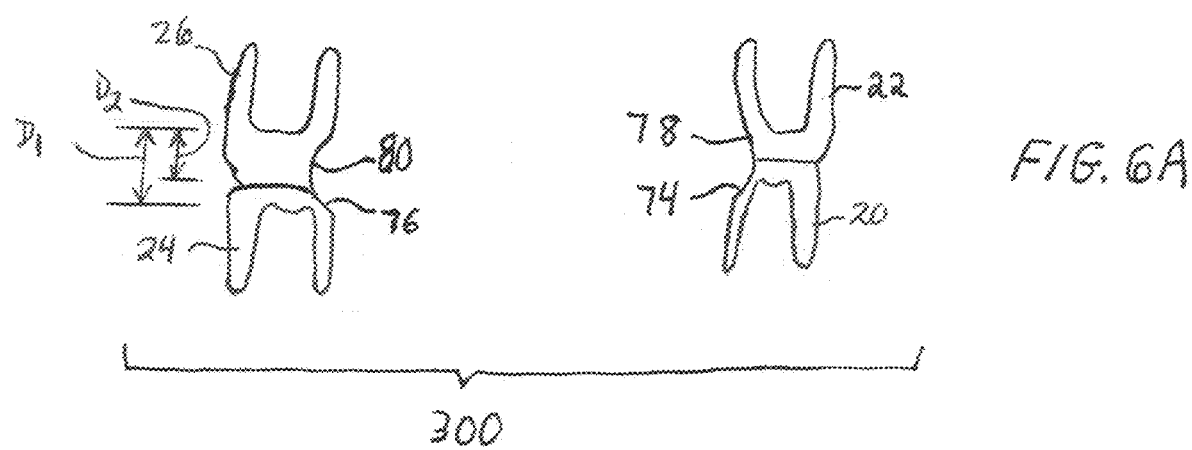

FIGS. 5, 6, and 6A illustrate schematically another embodiment 300, similar to embodiment 100, but rather than (or in addition to) featuring patterned surfaces, features curved interior surfaces 74, 76, 78, and 80, allowing more room for the user's tongue. The inventor herein has found that all users, but particularly those users with less than average size mouths may benefit in better sleep (with or without snoring reduction) by providing the user's tongue with even a small amount of extra room when the tongue relaxes. The inventor herein has found that even a few millimeters of lateral open space provides this advantage. As illustrated in FIGS. 6 and 6A, left-side lower curved surface 74 forms, with left-side upper curved surface 78, a left-side concavity, while right-side lower curved surface 76 forms, with right-side upper curved surface 80, a right-side concavity. Curved surfaces (sometimes referred to as arcuate surfaces) 74, 76, 78, and 80 may be formed after or formed integrally with during formation of their respective molar extensions 20, 24, 22, and 26. Distances D1 and D2 indicates thicknesses of the moldable or printable polymeric material, with thickness D1 being the total thickness of upper and lower trays and molar extensions, while thickness D2 is the thickness of only the upper tray and molar extensions. The ranges of values of thicknesses D1 and D2, as well as the range of the ratio D2/D1, were previously provided. Larger ratios within these ranges would be appropriate in all devices, but especially those that might include ramps, while smaller ratios in these ranges would be appropriate in all devices, but most especially in devices without ramps. FIG. 6A also illustrates that at least some users may have an offset between upper and lower molars, due to the upper jaw being larger than the mandible in some users. The offset may be referenced in terms of width of molars, and in some embodiments the offset may range from about ⅓ of a molar width to about ⅔ of molar width, or ⅓ of a molar tooth width to ⅔ of a molar tooth width.

Figure 8:
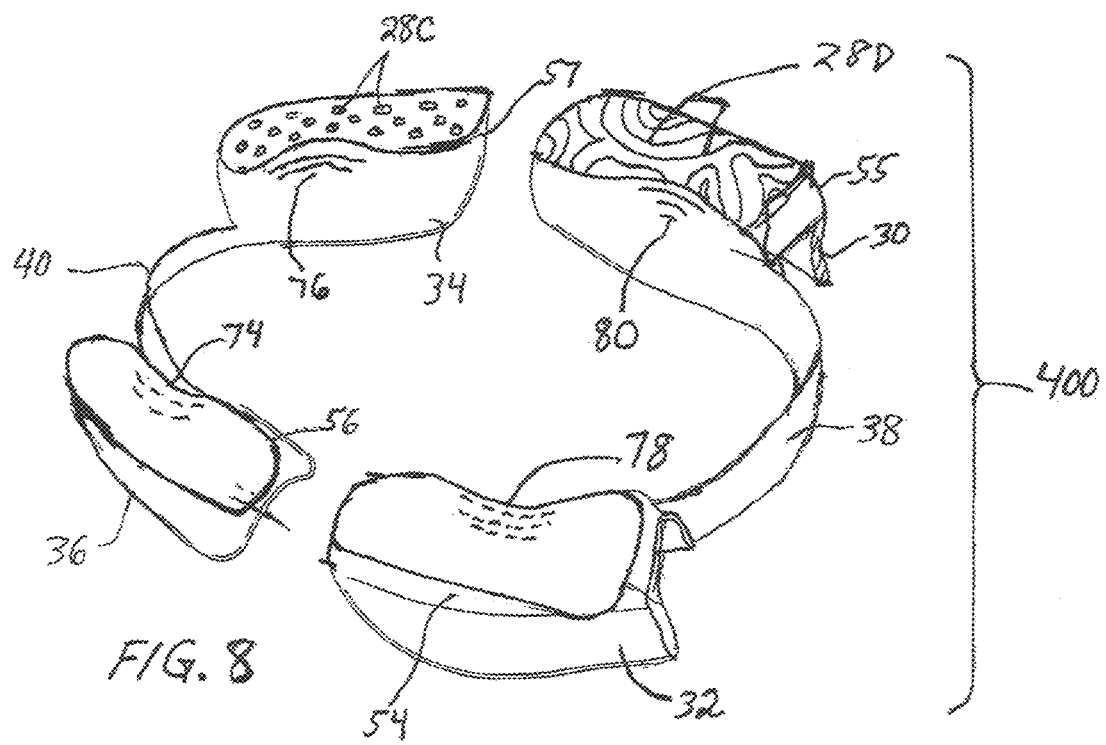
Figure 8A:
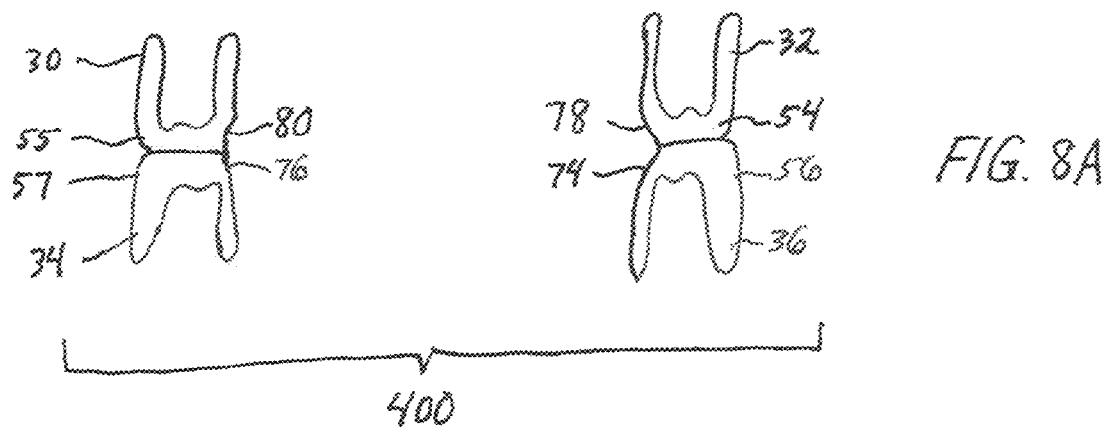

FIGS. 7, 8 and 8A illustrate schematically an embodiment 400 similar to embodiment 200, but rather than (or in addition to) featuring patterned surfaces, features a left-side lower curved surface 74 forming, with left-side upper curved surface 78, a left-side concavity, and a right-side lower curved surface 76 forming, with a right-side upper curved surface 80, a right-side concavity, as in embodiment 300. FIG. 8 emphasizes that certain embodiments may have both curved surfaces 74, 76, 78, and 80, as well as patterned surfaces, such as 28C, 28D. FIG. 8A illustrates a cross-sectional view of embodiment 400, without the patterned features 28C and 28D. FIGS. 7A and 7B illustrate embodiments 425 and 450, respectively, where the upper and lower trays are extended further than embodiment 400. In embodiment 425 (FIG. 7A), upper and lower trays extend over canines indicated at "C", and in embodiment 450 (FIG. 7B), upper and lower trays extend over canines "C" and lateral incisors "LI".

Figure 10:
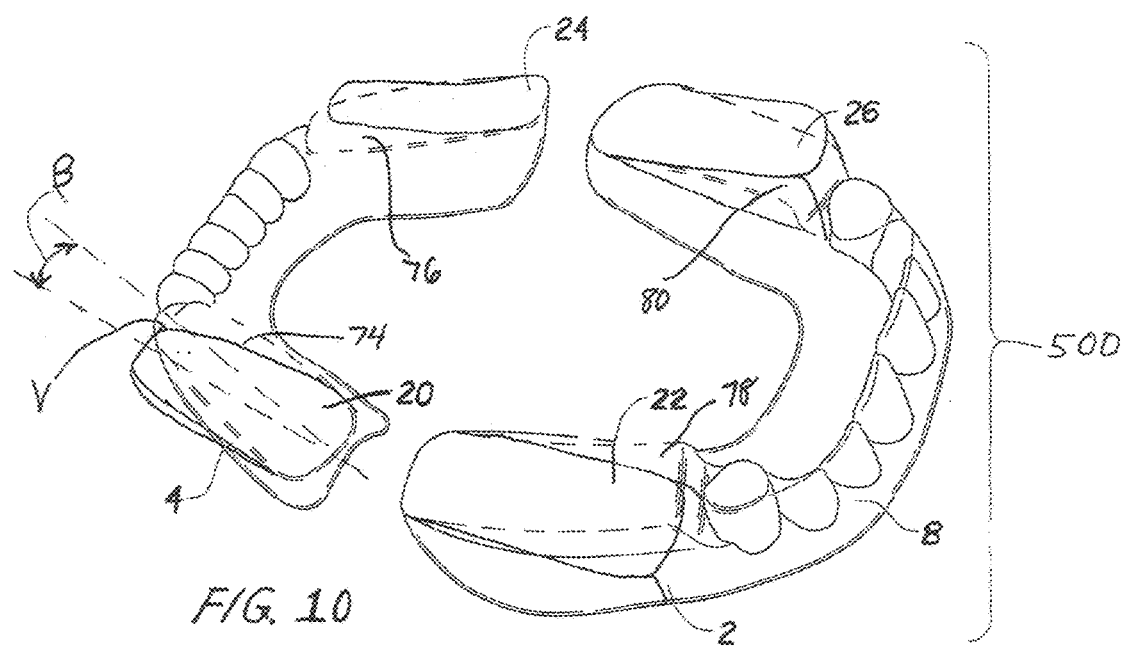
Figure 10A:
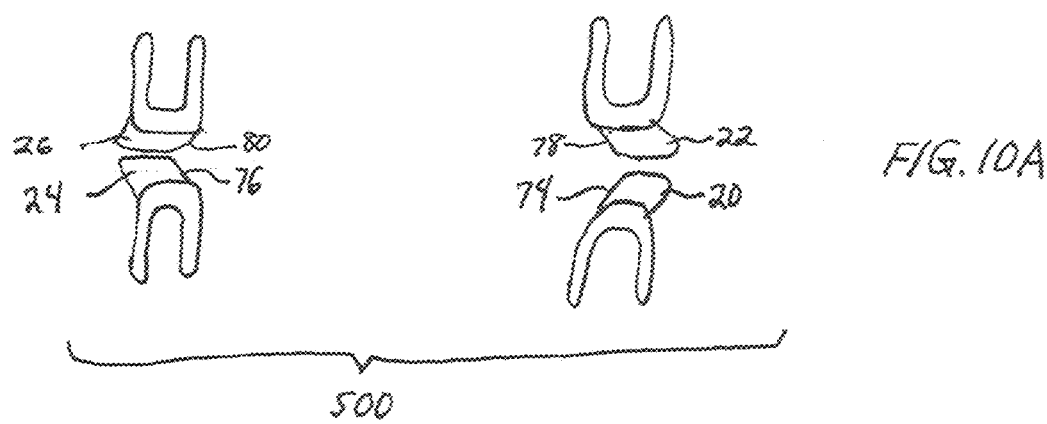
Figure 12:
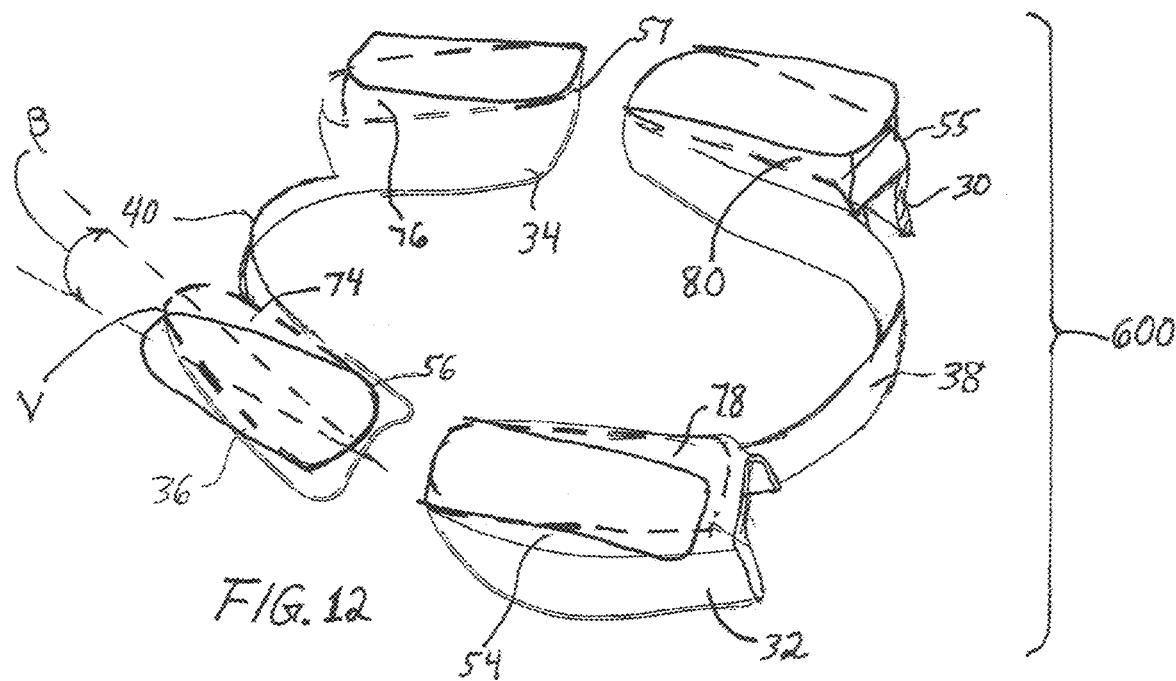
Figure 12A:
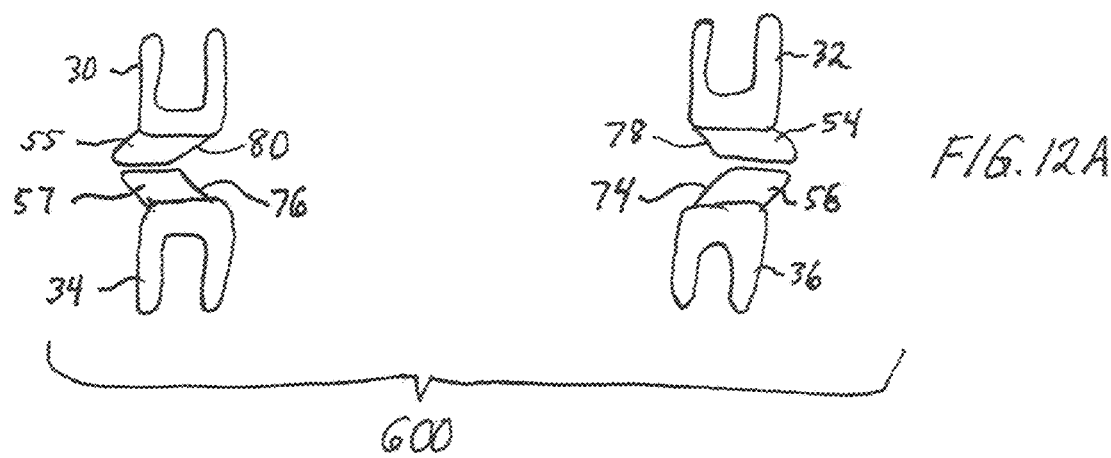

FIGS. 9, 10, and 10A illustrate an embodiment 500, and FIGS. 11, 12, and 12A illustrate an embodiment 600, each of which provides more room for a user's tongue as the tongue relaxes. This is accomplished by positioning the molar extensions, as illustrated in FIGS. 10 and 12, at an angle "β" to a generally longitudinal axis of trays 2, 4, in their respective molar regions. This positioning creates spaces or sub-chambers 74 (lower left), 76 (lower right), 78 (upper left), and 80 (upper right). Angle "β" may range from about 5 degrees to about 30 degrees, or from about 5 to about 25 degrees, or from about 10 to about 25 degrees. The original position of molar extensions is depicted by the dashed outlines. Sub-chambers 74, 78, themselves substantially prismatic in shape, form a larger prism-shaped left-side substantially prismatic-shaped chamber (combination of spaces formed by sub-chambers 74, 78), while sub-chambers 76, 80, themselves substantially prismatic in shape, form a larger prism-shaped right-side substantially prismatic-shaped chamber (combination of spaces formed by sub-chambers 76, 80). Only a few millimeters (about 1 to 5 mm, or about 1 to 3 mm, measured at the external vertex V (FIGS. 10 and 12) of a rough triangle formed by the dashed anterior line indicating original position of the molar extension and the angled, new position) of extra lateral space for the tongue may be required to have a significant effect on providing more space for the user's airway.

Figure 16:
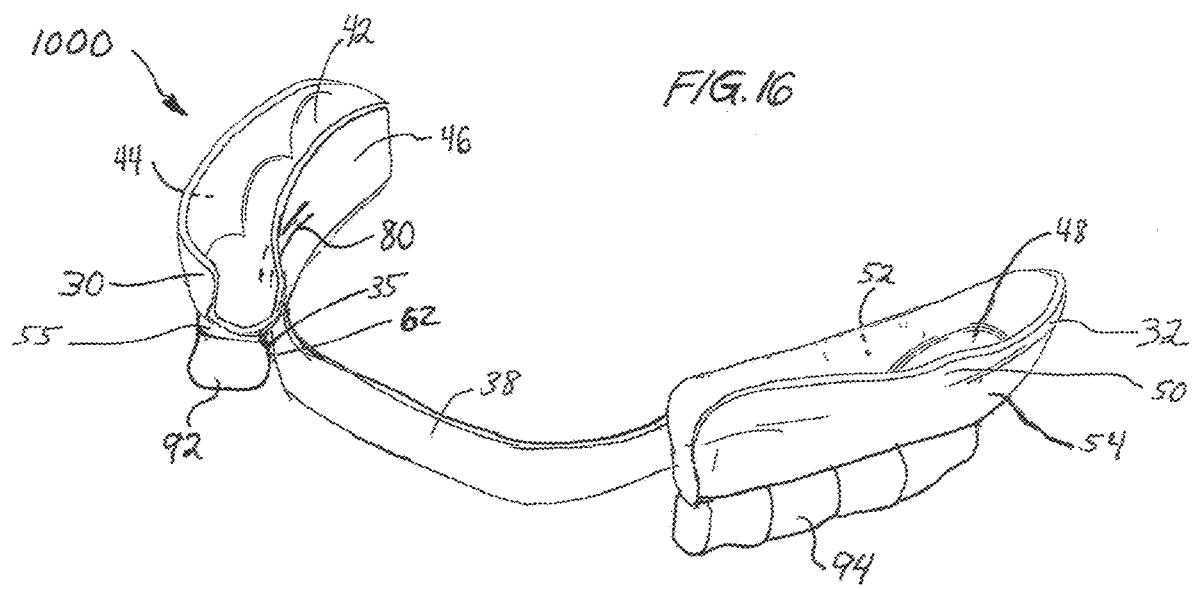
Figure 17:
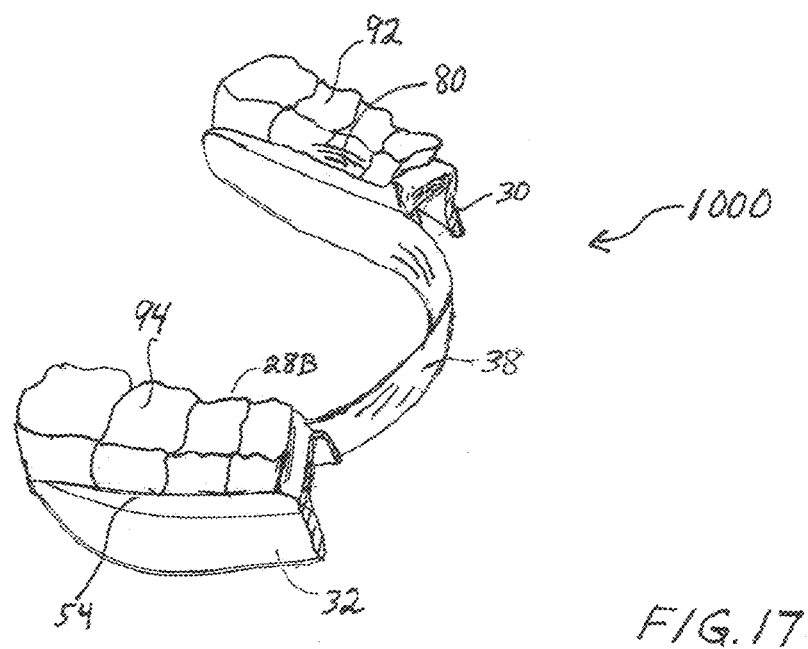

FIGS. 16 and 17 illustrate another oral device embodiment 1000 in accordance with the present disclosure which provides more room for a user's tongue as the tongue relaxes. This is accomplished by proving a second tier of pre-molar and molar extensions, as illustrated in FIGS. 16 and 17, at 92, 94. Second tiers 92, 94 may have curved interior surfaces, such exemplified by curved surface 80, allowing more space for a user's tongue upon relaxation, as in other embodiments described herein. Only a few millimeters (about 1 to 5 mm, or about 1 to 3 mm, measured laterally, provides extra space for the tongue and may be all that is required to have a significant effect on providing more space for the user's airway by providing more space for the tongue. The inventor has found that sleep may be significantly improved for certain users who may continue to snore. It should be emphasized that the second tiers 92, 94 may be added later to the pre-molar and molar extensions, or the second tiers 92, 94, may be formed at the same time as the pre-molar and molar extensions, such as during 3D printing of a software version of the oral device prepared from a pointcloud scanned image of a user's mouth and dentition. Second tiers 92, 94 may be identically shaped to a user's pre-molars and molars; in other words, second tier 92 may mimic the shape of pre-molars and molars adjacent generally U-shaped member 30, and second tier 94 may mimic the shape of pre-molars and molars adjacent generally U-shaped member 32.

It should be emphasized that left and right ramps as disclosed in my previous U.S. Patents and pending U.S. continuing patent application Ser. No. 16/416,234, filed May 19, 2019, may be employed, if desired or necessary for some users, in all embodiments of the devices of the present disclosure. These patents are expressly incorporated herein by reference: U.S. Pat. Nos. 9,144,515; 9,408,743; 9,439, 802; 9,445,938; and 10,299,957.

The materials of construction of the upper and lower general arch-shaped members, molar and premolar extensions, patterns, and alignment members may comprise any moldable or printable plastic (polymeric) material, or ceramic material, or metallic material, or combination thereof that is approved for use in oral medical devices and appliances for human use and that may be custom fitted for each user and tooth-retained via friction grip, and materials approved for animal use. The members may comprise a single material, or combination of materials. The members may comprise more than one layer of material, and each layer may be the same or different. The polymeric materials may be filled with various fillers, extenders, pigments, and other additives. In embodiments consisting essentially of moldable, biocompatible polymeric material, these fillers, extenders, pigments, and other additives are present in limited amounts to the extent necessary to substantially exceed minimum safety and effectiveness standards. Suitable polymeric materials include thermoplastics, thermosetting polymers, elastomers, and thermoplastic elastomers. The polymeric materials may comprise co-polymers, terpolymers, and blends of two or more chemical types of polymers, or blends of two or more polymers of the same chemical type, for example, a blend of two thermoplastics having different molecular weights.

Examples of specific polymers include polyacrylics, polyvinyls, polyvinyl alcohols, and the like. An example of a suitable polymeric material is a durable fade-proof acrylic that retains its shape and color for at least four-five years. Another example is made of a very pliable, soft, custom-injected silicone. Another example is a polymeric material compatible with home/office based bleaching techniques, such as the material used to make an OSAP device, and materials that can be molded into a ready-made semi-universal trial version, which may be suitable for patients who cannot endure having their impressions taken. In addition, the trial version is an inexpensive way to test a particular patients' tolerance to oral therapy. Another example is the material used in the device known under the trade designation SAGA. This device consists of a hard acrylic shell laminated to a soft vinyl liner. Another example is the acrylic material (Bruxeze™) that softens in hot water to provide a combination of comfort, strength, and retention, and which is used in the Adjustable PM Positioner™, an appliance that fits over all maxillary and mandibular teeth. Another example are the materials used in the device known as SomnoGuard® AP, which consists of an upper and a lower tray each made of two materials. The outer tray shells consist of solid clear and transparent medical grade polycarbonate. The inner lining which accommodates the teeth impressions is made of a thermoplastic copolymer. After the oral appliance is heated in a hot water bath its thermoplastic body molds easily to the teeth and jaws allowing any medical doctor to fit the device chair side. Yet another example is the material employed in the device known as SomnoGuard AP Pro®, which is a dental lab made two-part mandibular adjustable positioner to treat snoring and mild to moderate sleep apnea, and comprises common acrylic/elastomeric thermoform dental materials available in any dental lab after taking impressions of the lower and upper jaws and producing plaster models. Other polymeric materials that may be useful include nitinol, silicone, a PET, or any other biocompatible polymeric material. Other possible examples include PTFE, e-PTFE, polypropylene, polyurethane, polycarbonate, polyethylene terephthalate, stainless steel, titanium, tantalum, gold, polyvinidylene fluoride and combinations thereof "Biocompatibility" may be determined in accordance with national and/or international standards, such as ISO 10993.

The molar and premolar extensions may be integrally molded with their respective upper or lower generally arch-shaped members as illustrated schematically in the various figures using special molds, or may be made using additive manufacturing methods, such as 3D printing. In certain embodiments, one or more molding or printing steps may be required to build up the molar extensions, alignment members, and patterned surfaces to functional length and height. Also, the methods may include printing steps featuring specific polymers, colors, shapes, software, and the like.

Upper and lower trays, and various components, such as patterned surfaces, palatal bands, and second tier features as described herein may be made using a variety of additive and/or subtractive processes, including molding, machining, stamping and like additive processes, and/or subtractive processes such as net-shape casting (or near-net shape casting) using rapid prototype (RP) molds. Net-shape or near-net shape casting methods of making a variety of molds for producing a variety of complex products are summarized in patents assigned to 3D Systems, Inc., Rock Hill, South Carolina, U.S.A., for example U.S. Pat. No. 8,285,411. As summarized in the '411 patent, a number of technologies presently exist for the rapid creation of models, prototypes, and objects for limited run manufacturing. These technologies are generally called Solid Freeform Fabrication ("SFF") techniques. Some SFF techniques include stereolithography, selective deposition modeling, laminated object manufacturing, selective phase area deposition, multi-phase jet solidification, ballistic particle manufacturing, fused deposition modeling, particle deposition, laser sintering, film transfer imaging, and the like. Generally in SFF, complex parts are produced from a build material in an additive fashion as opposed to conventional fabrication techniques, which are generally subtractive in nature. For example, in most conventional subtractive fabrication techniques material is removed by machining operations or shaped in a die or mold to near net shape and then trimmed. In contrast, additive fabrication techniques incrementally add portions of a build material to targeted locations, layer by layer, in order to build a complex part. SFF technologies typically utilize a computer graphic representation of a part and a supply of a build material to fabricate the part in successive layers. According to the '411 patent, SFF technologies may dramatically shorten the time to develop prototype parts, can produce limited numbers of parts in rapid manufacturing methods, and may eliminate the need for complex tooling and machining associated with conventional subtractive manufacturing methods, including the need to create molds for custom applications. In addition, customized parts can be directly produced from computer graphic data (e.g., computer-aided design (CAD) files) in SFF techniques. Generally, in most techniques of SFF, structures are formed in a layer by layer manner by solidifying or curing successive layers of a build material. For example, in stereolithography a tightly focused beam of energy, typically in the ultraviolet radiation band, is scanned across sequential layers of a liquid photopolymer resin to selectively cure resin of each layer to form a multilayered part. In selective laser sintering, a tightly focused beam of energy, such as a laser beam, is scanned across sequential layers of powder material to selectively sinter or melt powder (such as a metal or ceramic powder) in each layer to form a multilayered part. In selective deposition modeling, a build material is jetted or dropped in discrete droplets, or extruded through a nozzle, such that the build material becomes relatively rigid upon a change in temperature and/or exposure to actinic radiation in order to build up a three-dimensional part in a layerwise fashion. In another technique, film transfer imaging ("FTI"), a film transfers a thin coat of resin to an image plane area where portions of the resin corresponding to the cross-sectional layer of the part are selectively cured with actinic radiation to form one layer of a multilayer part. Certain SFF techniques require the part be suspended from a supporting surface such as a build pad, a platform, or the like using supports that join the part to the supporting surface. Prior art methods for generating supports are described in U.S. Pat. Nos. 6,558,606; and 6,797,351. The Internet website of Quickparts.com, Inc., Atlanta, GA, a subsidiary of 3D Systems Inc., has more information on some of these techniques and materials that may be used.

Figure 13:
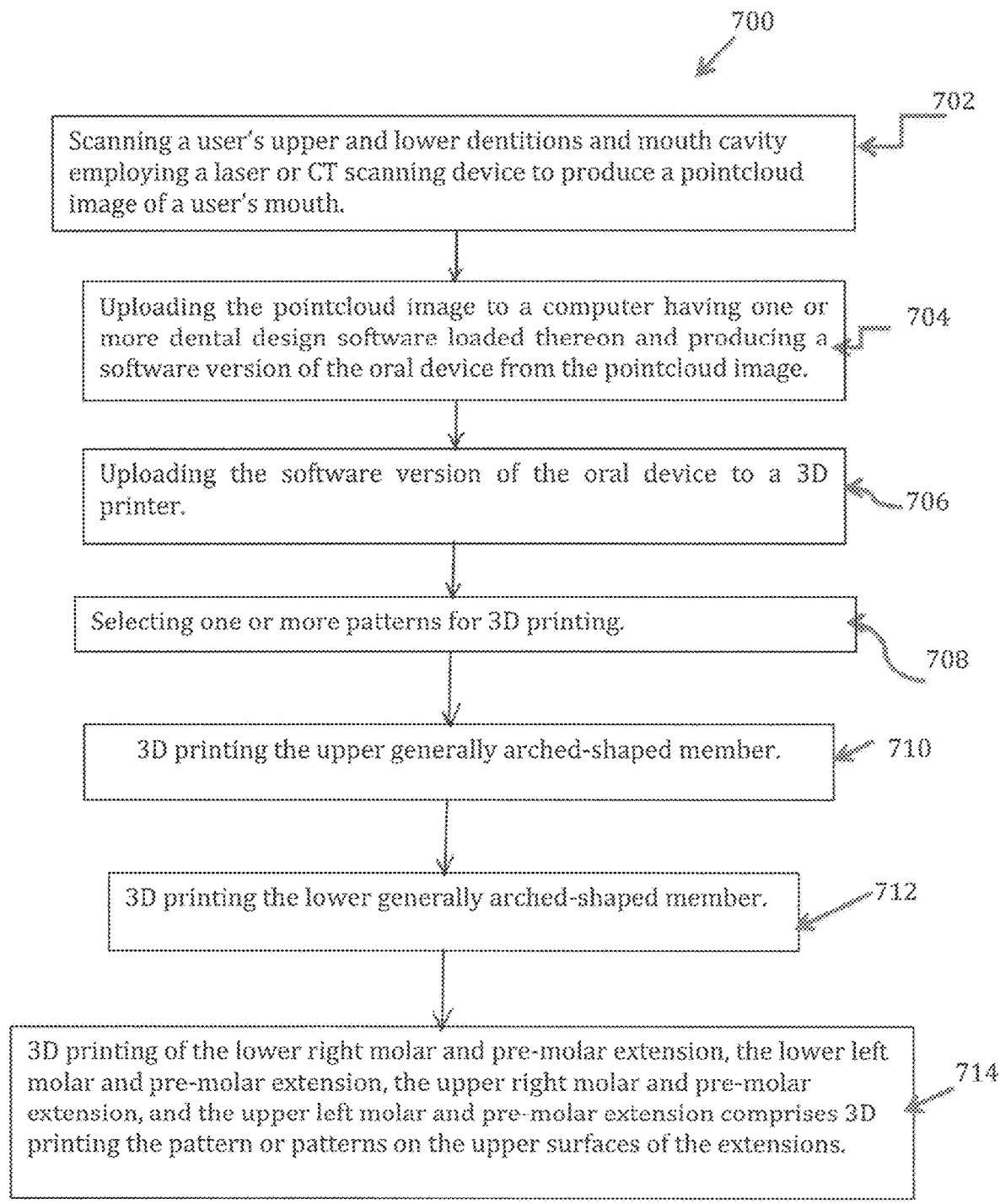
FIGS. 13, 14, and 15 are logic diagrams of three methods of making oral device embodiments of the present disclosure using additive manufacturing.
Figure 14:
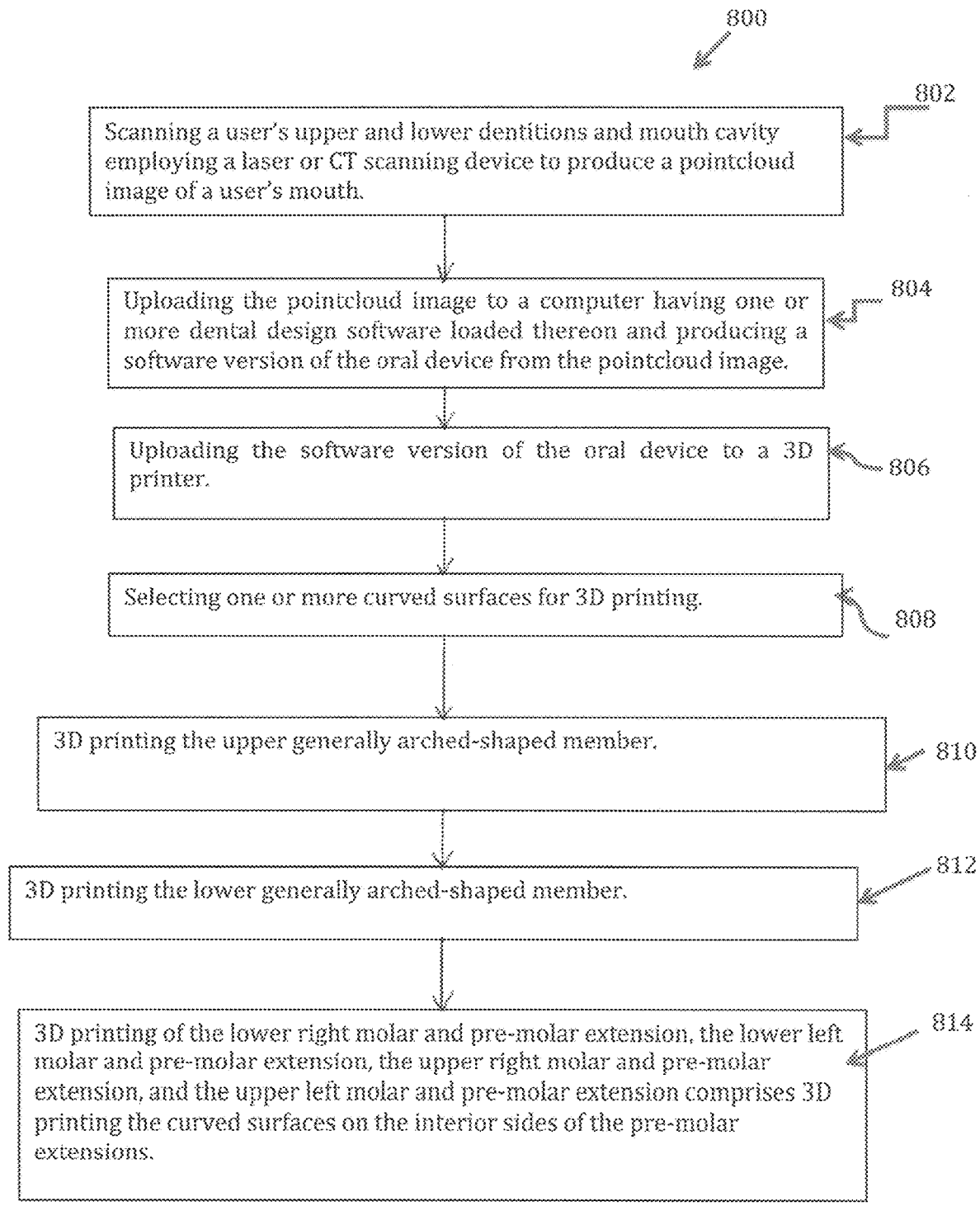
Figure 15:
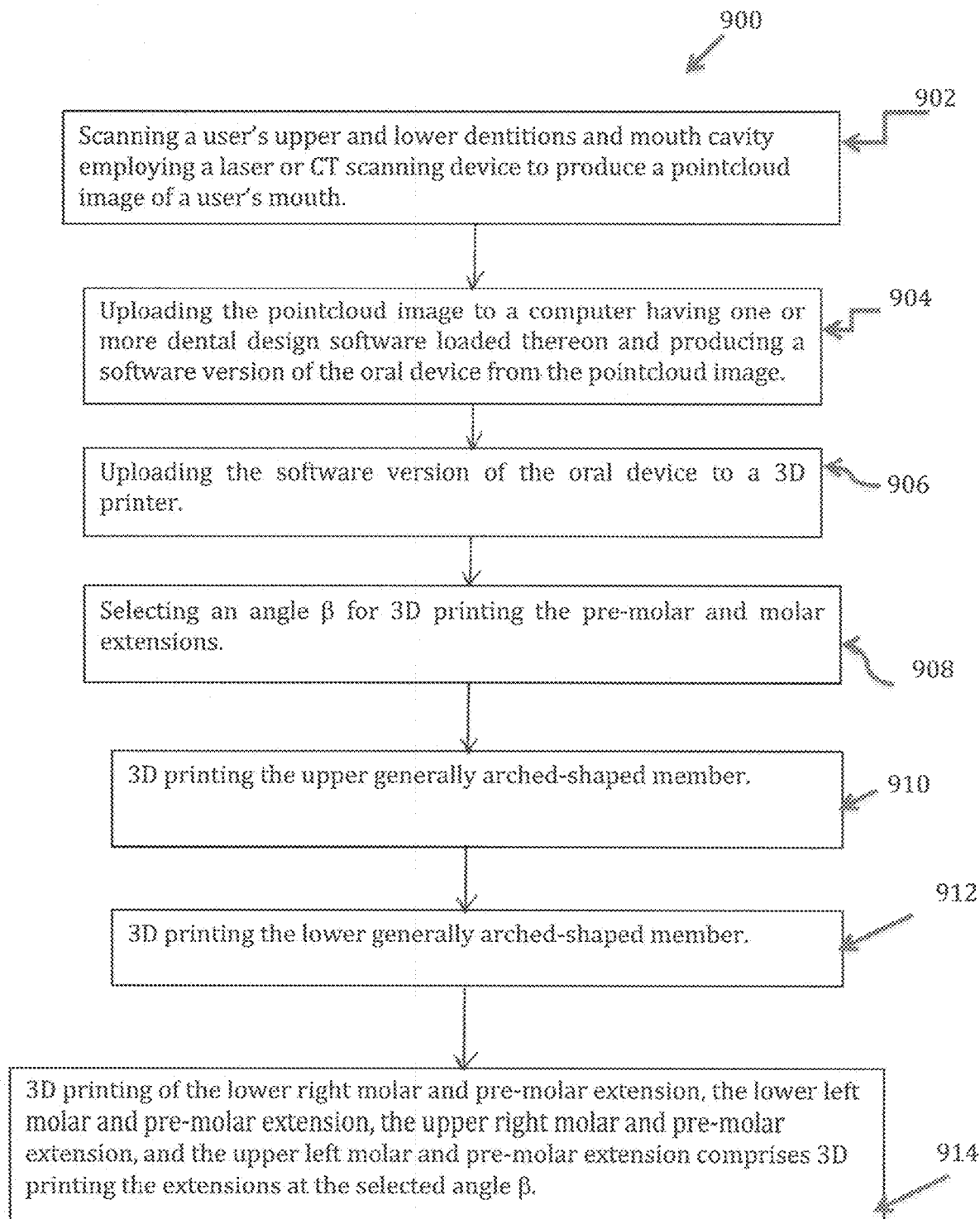

FIGS. 13, 14, and 15 are logic diagrams of three method embodiments 700, 800, and 900 of making an oral device of the present disclosure using additive manufacturing. Each method embodiment 700, 800, 900 comprises scanning a user's upper and lower dentitions and mouth cavity employing a laser or CT scanning device to produce a pointcloud image of a user's mouth (Boxes 702, 802, 902), uploading the pointcloud image to a computer having one or more dental design software programs loaded thereon or available remotely through an Internet connection, and producing a software version of the oral device from the pointcloud image (Boxes 704, 804, 904), and uploading the software version of the oral device to a 3D printer (Boxes 706, 806, 906). Method embodiment 700 comprises selecting one or more patterns for 3D printing (box 708), 3D printing the upper generally arched-shaped member (Box 710), 3D printing the lower generally arched-shaped member (Box 712); wherein the 3D printing of the lower right molar and pre-molar extension, the lower left molar and pre-molar extension, the upper right molar and pre-molar extension, and the upper left molar and pre-molar extension comprises 3D printing the pattern or patterns on the upper surfaces of the extensions (Box 714). Method embodiments 800 and 900 progress in similar fashion. In method embodiment 800, after uploading the pointcloud image of the user's mouth and producing a software version of the oral device (Box 804) and uploading the software version of the oral device to a 3D printer (box 806), method embodiment 800 comprises selecting one or more curved surfaces for 3D printing (box 808), 3D printing the upper generally arched-shaped member (Box 810), 3D printing the lower generally arched-shaped member (Box 812); wherein the 3D printing of the lower right molar and pre-molar extension, the lower left molar and pre-molar extension, the upper right molar and pre-molar extension, and the upper left molar and pre-molar extension comprises 3D printing the curved surfaces on the interior sides of the pre-molar extensions (Box 814). In method embodiment 900, after uploading the pointcloud image of the user's mouth (Box 904) and uploading the software version of the oral device to a 3D printer (Box 906), method embodiment 900 comprises selecting an angle R for 3D printing (box 908), 3D printing the upper generally arched-shaped member (Box 910), 3D printing the lower generally arched-shaped member (Box 912); wherein the 3D printing of the lower right molar and pre-molar extension, the lower left molar and pre-molar extension, the upper right molar and pre-molar extension, and the upper left molar and pre-molar extension comprises 3D printing the extensions at the selected angle (Box 914). Laser and CT scanning images is a well-established practice in the medical industry. See for example the laser and CT scanners available from Laser Design, Minneapolis, Minnesota (U.S.A.). See also U.S. Pat. Nos. 7,184,150; 7,153,135; and 9,522,054. In some cases, a 3D rendering may be made from a 2D image, such as a photograph or 2D drawing of a user's dentition. See for example U.S. Pat. Nos. 8,165,711 and 8,605,136. Intraoral imaging equipment, CAD/CAM and imaging analysis software are available from various sources, including Carestream Dental, 3 Shape, Renishaw, 3M, and others.

Although the foregoing description is intended to be representative of apparatus, kits, and methods in accordance with the present disclosure, it is not intended to in any way limit the scope of the appended claims. For example, rather than scanning the user's mouth and/or dentition using a laser scanner wand or CT scanner, the more traditional method of first making an impression of a person's teeth and jaw set may be made, and from that, a physical plaster model, or impression created. Once the physical model is made, a laser scanner or CT scanner may scan the physical model to produce the software version, which may then be used to mold or 3D print the oral devices of the present disclosure.

What is claimed is:

1. An oral device comprising:
   an upper generally arched-shaped member that is configured to fit adjacent at least a portion of interior and exterior surfaces of a user's upper dentition, the upper generally arched-shaped member comprising a first moldable or printable biocompatible polymeric material;
   a lower generally arched-shaped member that is configured to fit adjacent at least a portion of interior and exterior surfaces of a user's lower dentition, the lower generally arch-shaped member comprising a second moldable or printable biocompatible polymeric material, the first and the second moldable printable polymeric materials are the same or different;
   the lower generally arch-shaped member comprising a lower right molar and pre-molar extension and a lower left molar and pre-molar extension, each comprising a moldable or printable biocompatible polymeric material, the lower right and the lower left molar and pre-molar extensions formed integrally with and projecting generally perpendicularly away from the lower generally arch-shaped member and generally toward the upper generally arch-shaped member;
   the upper generally arch-shaped member comprising an upper right molar and pre-molar extension and an upper left molar and pre-molar extension, each comprising a moldable or printable biocompatible polymeric material, the upper right and upper left molar and pre-molar extensions formed integrally with and projecting generally perpendicularly away from the upper generally arch-shaped member and generally toward the lower generally arch-shaped member;
   so that when a user bites or clenches, the upper right molar and pre-molar extension impinges on the lower right molar and pre-molar extension, and the upper left molar and pre-molar extension impinges on the lower left molar and pre-molar extension;
   the upper and lower generally arch-shaped members having an anterior shape to form a gap sufficient for at least a portion of a user's tongue to extend forward into the gap without being impeded in forward movement by the device;
   the lower right molar and pre-molar extension, lower left molar and pre-molar extension, upper right molar and pre-molar extension, and upper left molar and pre-molar extension configured such that, when the apparatus is in a user's mouth, the molar extensions create a tendency to keep a user's airway open by maintaining the gap;

the lower right molar and pre-molar extension, lower left molar and pre-molar extension, upper right molar and pre-molar extension, and upper left molar and pre-molar extension each configured with arcuate interior surfaces such that, when the device is in the user's mouth, the arcuate interior surfaces create left and right sub-chambers allowing more room for a user's tongue; and the lower and the upper generally arch-shaped members are both lacking frontal vestibular upper and lower bands, but upper left and upper right portions are linked together by an upper frontal palatal band, and lower left and lower right portions are linked together by a lower frontal palatal band, wherein the upper frontal palatal band extends posterior along a portion of, or substantially all of a user's palate.

2. The oral device of claim 1 wherein the left and right sub-chambers are concave.

3. The oral device of claim 1 wherein the moldable or printable biocompatible polymeric material is selected from the group consisting of synthetic and natural materials.

4. The oral device of claim 1 wherein the first and second moldable or printable biocompatible polymeric materials are independently selected from the group consisting of polyurethanes, polysulfones, polycarboxylates, perfluorinated polymers, polyacrylics, polyvinyls, polyvinyl alcohols, silicones, polyolefins, and blends and copolymers thereof.

5. The oral device of claim 4 wherein first and second moldable or printable biocompatible polymeric materials are each selected from a durable fade-resistant acrylic that retains its shape and color for at least four years, and a very pliable, soft, custom-injected silicone.

6. An oral device comprising:

an upper generally arched-shaped member that is configured to fit adjacent at least a portion of interior and exterior surfaces of a user's upper dentition, the upper generally arched-shaped member comprising a first moldable or printable biocompatible polymeric material;

a lower generally arched-shaped member that is configured to fit adjacent at least a portion of interior and exterior surfaces of a user's lower dentition, the lower generally arch-shaped member comprising a second moldable or printable biocompatible polymeric material, the first and the second moldable printable polymeric materials are same or different;

the lower generally arch-shaped member comprising a lower right molar and pre-molar extension and a lower left molar and pre-molar extension, each comprising a moldable or printable biocompatible polymeric material, the lower right and the lower left molar and pre-molar extensions formed integrally with and projecting generally perpendicularly away from the lower generally arch-shaped member and generally toward the upper generally arch-shaped member;

the upper generally arch-shaped member comprising an upper right molar and pre-molar extension and an upper left molar and pre-molar extension, each comprising a moldable or printable biocompatible polymeric material, the upper right and upper left molar and pre-molar extensions formed integrally with and projecting generally perpendicularly away from the upper generally arch-shaped member and generally toward the lower generally arch-shaped member;

so that when a user bites or clenches, the upper right molar and pre-molar extension impinges on the lower right molar and pre-molar extension, and the upper left molar and pre-molar extension impinges on the lower left molar and pre-molar extension;

the upper and lower generally arch-shaped members having an anterior shape to form a gap sufficient for at least a portion of a user's tongue to extend forward into the gap without being impeded in forward movement by the device;

the lower right molar and pre-molar extension, lower left molar and pre-molar extension, upper right molar and pre-molar extension, and upper left molar and pre-molar extension configured such that, when the apparatus is in a user's mouth, the molar extensions create a tendency to keep a user's airway open by maintaining the gap; and the lower and the upper generally arch-shaped members are both lacking frontal vestibular upper and lower bands, but upper left and upper right portions are linked together by an upper frontal palatal band, and lower left and lower right portions are linked together by a lower frontal palatal band, wherein the upper frontal palatal band extends posterior along a portion of, or substantially all of a user's palate.

7. The oral device of claim 6 wherein the first and second moldable or printable biocompatible polymeric materials are independently selected from the group consisting of polyurethanes, polysulfones, polycarboxylates, perfluorinated polymers, polyacrylics, polyvinyls, polyvinyl alcohols, silicones, polyolefins, and blends and copolymers thereof.

8. The oral device of claim 7 wherein first and second moldable or printable biocompatible polymeric materials are each selected from a durable fade-resistant acrylic that retains its shape and color for at least four years, and a very pliable, soft, custom-injected silicone.

* * * * *